(12) United States Patent
Itagaki et al.

(10) Patent No.: US 6,546,274 B2
(45) Date of Patent: Apr. 8, 2003

(54) MAGNETIC RESONANCE IMAGING METHOD AND APPARATUS

(75) Inventors: Hiroyuki Itagaki, Hachioji (JP); Hisaaki Ochi, Kodaira (JP)

(73) Assignee: Hitachi Medical Corporation, Tokyo (JP)

( * ) Notice: Subject to any disclaimer, the term of this patent is extended or adjusted under 35 U.S.C. 154(b) by 86 days.

(21) Appl. No.: 09/788,512

(22) Filed: Feb. 21, 2001

(65) Prior Publication Data

US 2001/0018559 A1 Aug. 30, 2001

(30) Foreign Application Priority Data

Feb. 22, 2000 (JP) .......................... 2000-050454

(51) Int. Cl.$^7$ ................................. A61B 5/05
(52) U.S. Cl. ................ 600/413; 600/410; 600/428; 324/307; 324/309; 324/314
(58) Field of Search ............... 600/410, 413; 324/307, 309; 128/653

(56) References Cited

U.S. PATENT DOCUMENTS

| | | | | |
|---|---|---|---|---|
| 4,307,344 A | * | 12/1981 | Walters | 324/307 |
| 5,054,489 A | * | 10/1991 | Axel et al. | 600/419 |
| 5,126,673 A | * | 6/1992 | Hennig | 324/309 |
| 5,212,448 A | * | 5/1993 | Le Roux et al. | 324/307 |
| 5,379,766 A | * | 1/1995 | McKinnon et al. | 318/686 |
| 5,544,652 A | * | 8/1996 | Duyn | 324/309 |
| 5,789,922 A | * | 8/1998 | Ochi et al. | 324/309 |

OTHER PUBLICATIONS

McVeigh, E. and Zerhouni, E., A rapid starburst pulse sequence for cardiac tagging. Book of Abstracts, Society for Magnetic Resonance in Medicine (SMRM), Amsterdam, 1989, p. 23.*
Axel, L. et al., MR imaging of motion with spatial modulation of magnetization, Radiology, vol. 171 :841–845 (1985).*
Axel, L. et al., Heart wall motion: improved method of spatial modulation of magnetization for MR imaging, Radiology, vol. 172:349–350 (1989).*
Matthaei, D. et al., Cardiac and vascular imaging with an MR snapshot technique, Radiology, vol. 177:527–532 (1990).*

* cited by examiner

Primary Examiner—Marvin M. Lateef
Assistant Examiner—Barry Pass
(74) Attorney, Agent, or Firm—Antonelli, Terry, Stout & Kraus, LLP

(57) ABSTRACT

A nuclear magnetic resonance imaging apparatus in which a synchronizing signal is generated from a periodic physiological signal generated by a subject to be inspected, and a radiofrequency burst pulse is applied to the subject to be inspected in synchronism with the synchronizing signal while a gradient magnetic field in one direction is being applied to the subject to be inspected to modulate nuclear magnetizations of the subject to be inspected in the one direction. The radiofrequency burst pulse includes plural sub-pulses which are formed at equidistant intervals on a time axis and which have amplitudes modulated by a sinc function.

20 Claims, 25 Drawing Sheets

MAGNETIC RESONANCE IMAGING METHOD AND APPARATUS

BACKGROUND OF THE INVENTION

This invention relates to a magnetic resonance imaging apparatus (referred to hereafter as MRI), and in particular to a magnetic resonance imaging apparatus which performs imaging by assigning magnetic tags, and a magnetic resonance imaging method.

The terminology used in the following description of this specification is summarized below.

[Tagging Sequence]: Sequence for applying magnetic field which performs magnetic tagging (pulse sequence).

[Imaging Sequence]: Sequence for applying magnetic field which performs magnetic resonance imaging (MRI) (pulse sequence).

[Amplitude Modulated Burst Pulse]: Radiofrequency burst pulse comprising plural sub-pulses formed at equal intervals on the time axis whereof the amplitudes are modulated by a sinc function (the plural sub-pulses comprise a sub-pulse of amplitude value 0).

[Period in Cardiac Cycle]: The times when one cardiac cycle is divided into for example, approximately, 4–12 parts when extracting the amount of movement of the heart wall.

[Echo Signal Gathering Efficiency]: Number of echo signals gathered in unit time.

First, the prior art technology will be described regarding analysis of cardiac function by performing magnetic tagging to image the motion of the heart wall (Ref. 1: L. Axel et al., MR Imaging of Motion with Spatial Modulation of Magnetization: Radiology, vol. 171, p. 841–845 (1989)).

FIG. 17 is a diagram describing the principle of assigning magnetic tags disclosed in Ref. 1. FIG. 17A is a diagram describing a tagging sequence. FIG. 17B is a diagram describing the behavior of magnetization vectors in the tagging sequence of FIG. 17A, and FIG. 17C is a diagram describing the spatial intensity distribution of the z direction component of the nuclear magnetization vector.

In FIG. 17, a static magnetic field is applied in the z direction. As shown in FIG. 17B, in the initial state (time 0) shown in FIG. 17A, the nuclear magnetization vector is oriented in the z direction, and as shown in FIG. 17C, the intensity of the z direction component of the nuclear magnetization vector is M0 (constant value). As shown in FIG. 17A, when a radiofrequency magnetic field pulse RF is irradiated at a time a, the nuclear magnetization vector rotates around the x axis and inclines at an angle θ in the yz plane, and the intensity of the z direction component of the nuclear magnetization vector is M0 cos θ. Next, as shown in FIG. 17A, when a gradient magnetic field Gx is applied at a time b, the nuclear magnetization vector is phase-modulated corresponding to the position coordinates.

FIG. 18 is a diagram describing the intensity of the x direction component of the nuclear magnetization vector in a tagging sequence according to the prior art. As shown in FIG. 18, the intensity of the x direction component of the nuclear magnetization vector after applying the inclined magnetic field Gx is modulated relative to the x direction in which the gradient magnetic field Gx is applied. However, as shown in FIG. 17C, the intensity of the z direction component of the nuclear magnetization vector is M0 cos θ (constant value). The nuclear magnetization vector precesses around the z axis.

Subsequently, as shown in FIG. 17A, when the radiofrequency magnetic field pulse RF is again irradiated at a time c, the nuclear magnetization vector rotates around the x axis, and inclines at an angle θ in the yz plane. As a result, the modulation in the x direction of the nuclear magnetization vector shown in FIG. 18 is reflected in the z direction component of the nuclear magnetization vector. Due to the tagging sequence described above, as shown in FIG. 17C, at a time d before the imaging sequence is implemented, the z direction component of the nuclear magnetization vector can be modulated corresponding to the x coordinate.

When the imaging sequence is implemented, the above spatial modulation of the z direction component of the nuclear magnetization vector is reflected in the signal intensity of the acquired image, and stripes are generated perpendicular to the x direction on the image. Specifically, magnetization is suppressed in the peripheral part of the stripes on the image obtained by the tagging sequence shown in FIG. 17A. By a combination of the applied amount and applied direction of the gradient magnetic field, the direction of the stripes and interval of the stripes can be controlled, and stripes can also be generated in the vertical and horizontal directions. These stripes are tags.

FIG. 19 is a diagram describing the tagging sequence in the prior art. In FIG. 17, the simplest example has been shown to describe the principle of tagging, but in general, a binomial SPAMM (Spatial Modulation of Magnetization) pulse which makes the amplitude ratio of the radiofrequency magnetic field pulses RF3', 5' a binomial coefficient is often used (Ref. 2: L. Axel, et al., Heart Wall Motion: Improved Method of Spatial Modulation of Magnetization for MR Imaging, Radiology, vol. 172, p. 349–350 (1989)), as shown in FIG. 19. The numbers above the radiofrequency magnetic field pulse RF shown in FIG. 19 are amplitude ratios of radiofrequency magnetic field pulses.

In the example shown in FIG. 19, a gradient magnetic field Gx4' in the x direction is applied alternately with a radiofrequency magnetic field pulse RF3', a gradient magnetic field Gx6' in the y direction is applied alternately with a radiofrequency magnetic field pulse RF5', and tags are assigned in the x direction and y direction. As described hereabove, if the method disclosed in Ref. 1 is used, the nuclear magnetization is suppressed at equal intervals in straight lines in the vertical and horizontal directions, i.e. in a grid shape. As a result, if the imaging sequence is implemented immediately after completion of the tagging sequence, an MRI image is obtained having bright points arranged in a lattice.

In general, a pulse sequence according to a fast imaging method is used as the imaging sequence, particularly the pulse sequence in the fast spin echo technique (Ref. 3: D. Matthaei et al., Cardiac and Vascular Imaging with an MR Snapshot Technique, Radiology, vol. 177, pp. 527–532 (1990)). The fast spin echo technique is suitable for extraction of the heart wall. It may be mentioned that the echo planar (EPI) technique is suited to extraction of blood circulation, but not to extraction of the heart wall.

FIG. 25 is a diagram describing the imaging sequence in the prior art. FIG. 25A is fast spin echo type pulse sequence wherein a radiofrequency burst pulse, comprising plural sub-pulses formed at equidistant intervals on the time axis whereof the amplitudes are modulated by a sinc function, is applied. FIG. 25B shows a pulse sequence according to the fast spin echo method.

In the pulse sequence shown in FIG. 25A, after a first amplitude modulated burst pulse is irradiated, a slice gradient magnetic field Gs is applied, a π pulse is irradiated, and slice selection and inversion of magnetization are performed. Next, a readout gradient magnetic field Gr is applied, the phase of the nuclear magnetization is provided to generate an echo signal, and the echo signal is measured. Subsequently, inversion of magnetization due to irradiation by the π pulse and application of the readout gradient magnetic field following the π pulse are repeated to generate echo signals on plural occasions, and measurement of the echo signal is repeated. The number of echo signals generated by one irradiation with the π pulse is equal to the number of sub-pulses in the first amplitude modulated burst pulse. It should be noted that different phase encodings are assigned to the echo signals by a phase encoding gradient magnetic field Gp.

In the pulse sequence (imaging sequence) shown in FIG. 25A, after a second amplitude modulated burst pulse is irradiated wherein the carrier frequency of the first amplitude modulated burst pulse is shifted, a π pulse is irradiated and the echo signal is measured in the same way as following the first amplitude modulated burst pulse. In the example shown in FIG. 25A, five echo signals are generated for each irradiation of a π pulse. However, only the most important echo signals may be gathered considering the SN ratio and echo signal measuring time.

In the pulse sequence shown in FIG. 25B, the slice gradient magnetic field Gs is applied, a π/2 pulse is irradiated, a slice is selected, and the readout gradient magnetic field Gr is applied to disperse the phase of the nuclear magnetization. Next, the slice gradient magnetic field Gs is applied, the π pulse is irradiated to invert the nuclear magnetization, the readout gradient magnetic field Gr is applied, the phase of the nuclear magnetization is provided to generate an echo signal, and the echo signal is measured.

Subsequently, the slice gradient magnetic field Gs is applied, inversion of nuclear magnetization with irradiation of the π pulse and application of the readout gradient magnetic field are repeated, an echo signal is generated on plural occasions, and measurement of the echo signal is repeated. It should be noted that different phase encodings are assigned to the echo signals by the phase encoding gradient magnetic field Gp.

FIG. 20 is a diagram describing the pulse sequence in a prior art MRI apparatus wherein tagging is performed and the motion of the heart wall is imaged. Hereafter, the method of detecting the motion of the heart wall will be described using FIG. 20. Information regarding the motion of the heart wall is obtained by modifying the start time of an imaging sequence 40. For example, a synchronizing signal 2 is output at which an R wave 1 of an electrocardiogram is maximized, a tagging sequence 30 is performed at a time t0 immediately after input of the synchronizing signal, and the imaging sequence 40 is begun at a time t1. Next, the tagging sequence 30 is implemented at the time t0 immediately after the synchronizing signal 2 detected from the R wave of the electrocardiogram, and the MRI image is acquired by modifying only the start time of the imaging sequence 40, i.e., t1, t2, t3 . . .

Herein, if for example the MRI image 1 obtained if the imaging sequence is started at the time t1 and the MRI image 2 obtained if the imaging sequence is started at the time t2 are compared, the positions of the bright spots on the image vary. The displacement amount of the bright spots of the tags reflects the displacement amount of the heart wall from the time t1 to the time t2. Using plural MRI images obtained by modifying the start time of the imaging sequence, i.e., t1, t2, t3 . . . the amount of movement of the heart wall and the speed of motion of the heart wall, which are important parameters in evaluating cardiac function, can be extracted.

In the prior art for imaging the movement of the heart using tags, there are two problems. The bright spots of the tags are obtained by suppressing the signal at the periphery, so the larger the time interval from completion of the tagging sequence to start of the imaging sequence, the better the recovery of the suppressed nuclear magnetization. In general, the recovery time is longer in the case the magnetization is suppressed more strongly. At the time d shown in FIG. 17C, the larger the intensity difference between the broken line representing signal intensity prior to modulation and the solid line representing signal intensity after modulation, the longer the recovery time required. Here, it is seen that if bright spots are represented by the area of the signal intensity M0, the nuclear magnetization recovers in a short time in its vicinity. In other words, the larger the time interval up to start of the imaging sequence, the larger the size of the bright spots due to recovery of nuclear magnetization. This is the phenomenon referred to as blurring of the bright spots. If the bright spots are blurred, identification of the bright spots of the tags is difficult, and the precision involved in extracting the amount of movement of the heart wall declines.

To extract the amount of movement of the heart wall, an MRI image is generated in each period of the cardiac cycle. If a new dimension, i.e. the period of the cardiac cycle, is added to the number of dimensions of an ordinary MRI image (e.g., 2 dimensions for a flat image), the subject has to be restrained for a long time. For example, the imaging time for one slice in the prior art imaging technique is 32 seconds. If there are 12 slices and the period of the cardiac cycle is divided into 12 parts, the subject must be restrained for at least 70 minutes to acquire an image, and this is stressful for the subject.

A technique was therefore desired to resolve the above problems and extract the cardiac function to high precision in a short time.

SUMMARY OF THE INVENTION

It is therefore an object of this invention to provide a magnetic resonance imaging apparatus which can apply an amplitude modulated burst pulse and gradient magnetic field in a predetermined sequence, modify nuclear magnetization vectors corresponding to positional coordinates to assign tags, acquire an MRI image, and extract a cardiac function to high precision in a short time.

According to this invention, an amplitude modulated burst pulse comprising plural sub-pulses formed at equidistant intervals on the time axis whereof the amplitudes are modulated by a sinc function ($\{\sin(t)\}/t$), is used as an excitation radio frequency magnetic field pulse for a tagging sequence which performs tagging, and an imaging sequence which performs imaging of a magnetic resonance image. According to this invention, tags where blurring of bright spots is small can be assigned in at least one direction, and imaging can be performed in a short time. Also, according to this invention, a cardiac function analysis can for example be performed which quantitatively evaluates the pump function of the heart by detecting the motion of the heart wall. Hereafter, the representative features of the invention will be described.

The nuclear magnetic resonance imaging apparatus of this invention comprises a static magnetic field generating means in which a subject to be inspected is placed, a gradient magnetic field of generating means which generates a gradient magnetic field in three (first, second and third) perpendicular directions, a radiofrequency magnetic field generating means which generates a radiofrequency magnetic field, a signal detecting means which detects a nuclear magnetic resonance signal generated from the subject to be inspected, and a physiological signal detecting means which detects a periodic physiological signal from the subject to be inspected. It further comprises a control means which controls the gradient magnetic field generating means, radiofrequency magnetic field generating means, signal detecting means and physiological signal detecting means, and performs control to implement a predetermined pulse sequence.

The control means (1) detects a physiological signal based on respiration or heartbeat, etc., and generates a synchronizing signal which initiates a pulse sequence which detects a nuclear magnetic resonance signal (echo signal) from the physiological signal.

In a first construction of the nuclear magnetic resonance apparatus of this invention, the control means further (2) synchronizes a first radiofrequency burst pulse (first amplitude modulated burst pulse) comprising plural sub-pulses formed at equidistant intervals on the time axis whereof the amplitudes are modulated by a sinc function and the gradient magnetic field in one direction (first or second direction) of the three directions with the synchronizing signal, applies them, modulates the nuclear magnetization of the subject to be inspected in one direction, and controls the tagging sequence in one direction.

In a second construction of the nuclear magnetic resonance apparatus of this invention, the control means further (2) synchronizes the first radiofrequency burst pulse (first amplitude modulated burst pulse) comprising plural sub-pulses formed at equidistant intervals on the time axis whereof the amplitudes are modulated by a sinc function and the gradient magnetic field in the first direction, applies them, modulates the nuclear magnetization of the subject to be inspected in the first direction, and (3) applies a second radiofrequency burst pulse (second amplitude modulated burst pulse) comprising plural sub-pulses formed at equidistant intervals on the time axis whereof the amplitudes are modulated by a sinc function and the gradient magnetic field in the second direction, modulates the nuclear magnetization of the subject to be inspected in the second direction, and controls the tagging sequence in the first and second directions.

In the aforesaid first and second constructions, the nuclear magnetization of the subject in a rectangular periodic region is excited, so compared to modulation of nuclear magnetization by a trigonometric function in the tagging of the prior art, tags with much less blurring of bright spots can be assigned. As a result, the movement and thickness deformations of the heart wall and valves in one or two dimensions can be measured to high precision from the image reconstructed from the echo signals measured by the imaging sequence performed after the tagging sequence.

In a third construction of the nuclear magnetic resonance imaging apparatus of this invention, in addition to (1) and (2) of the first construction, the control means (3) applies the second radiofrequency burst pulse (second amplitude modulated burst pulse) comprising plural sub-pulses formed at equidistant intervals on the time axis whereof the amplitudes are modulated by a sinc function and the gradient magnetic field in the first direction to excite the nuclear magnetization of the subject to be inspected after a predetermined waiting time has elapsed following implementation of (2), (4) applies a radiofrequency magnetic field pulse while a gradient magnetic field is applied in the third direction, (5) assigns positional information in the second direction to the nuclear magnetization due to application of the gradient magnetic field in the second direction, generates a nuclear magnetic resonance signal in which positional information in the first direction is assigned to the nuclear magnetization due to application of the gradient magnetic field in the first direction, and measures the nuclear magnetic resonance signal, (6) repeats the steps (4) and (5) plural times, and (7) repeats the steps from (1) to (6) plural times. Further, in the third construction, images of the heart are reconstructed in the same period of the cardiac cycle or different periods of the cardiac cycle by performing (7) where the aforesaid predetermined waiting time is constant, and by varying the predetermined waiting time on each occasion the steps (1) to (6) in (7) are repeated.

In a fourth construction of the nuclear magnetic resonance imaging apparatus of this invention, in addition to (1), (2) and (3) of the second construction, the control means (4) applies a third radiofrequency burst pulse (third amplitude modulated burst pulse) comprising plural sub-pulses formed at equidistant intervals on the time axis whereof the amplitudes are modulated by a sinc function and the gradient magnetic field in the first direction to excite the nuclear magnetization of the subject to be inspected after a predetermined waiting time has elapsed following implementation of (3), (5) applies a radiofrequency magnetic field pulse while a gradient magnetic field is applied in the third direction, (6) assigns positional information in the second direction to the nuclear magnetization due to application of the gradient magnetic field in the second direction, generates a nuclear magnetic resonance signal in which positional information in the first direction is assigned to the nuclear magnetization due to application of the gradient magnetic field in the first direction, and measures the nuclear magnetic resonance signal, (7) repeats the steps (5) and (6) plural times, and (8) repeats the steps from (1) to (7) plural times. Further, in the fourth construction, images of the heart are reconstructed in the same period of the cardiac cycle or different periods of the cardiac cycle by performing (8) where the aforesaid predetermined waiting time is constant, and by varying the predetermined waiting time on each occasion the steps (1) to (7) in (8) are repeated.

In the aforesaid third and fourth constructions, the nuclear magnetization of the subject in a rectangular periodic region is excited, the width of the rectangular periodic region is larger than the size of the pixels of the image reconstructed from the measured echo signal, the width of the rectangular periodic region is an integral number of times the size of the pixels of the reconstructed image, and the edge of the rectangular periodic region coincides with the boundary line between pixels of the reconstructed image. Therefore, compared to modulation of the nuclear magnetization by a trigonometric function with tags of the prior art, tags with much less blurring of bright spots can be assigned, and the image can be acquired in a short time. As a result, the movement and thickness deformations of the heart wall and valves in one or two dimensions can be measured to high precision from the reconstructed image, and useful information regarding heart disease can be obtained.

According to the aforesaid third and fourth constructions, the second and third amplitude modulated burst pulses are irradiated to perform fast image acquisition. In this invention, an imaging sequence is performed which excites nuclear magnetization at n (in general, n is the number of exponentiations of 2) frequencies, and an echo signal can be detected when the nuclear magnetization in the imaging cross-section containing the subject to be inspected is excited in a substantially uniform manner (Ref 4: U.S. Pat. No. 5,789,922).

The characteristic feature of this invention is that a radiofrequency burst pulse (amplitude modulated burst pulse) comprising plural sub-pulses formed at equidistant intervals on the time axis whereof the amplitudes are modulated by a sinc function, is applied with a pulse sequence which is at least one of a tagging sequence and an imaging sequence.

The application of this amplitude modulated burst pulse will now be summarized.

FIG. 22 is a diagram describing an amplitude modulated burst pulse of the prior art. The amplitude modulated burst pulse comprises plural sub-pulses whereof the amplitudes are modulated by a sinc function (period T), and the shape of the sub-pulses is a sinc function. Including the sub-pulse for which the amplitude value is 0, the interval between sub-pulses on the time axis is τ.

FIG. 23 is a diagram describing the relation between impulse sequences in a real space and in a frequency space. A series of impulses (δ function series 1) having a fixed interval τ on the time axis of real space and a series of impulses (δ function series 2) having a fixed interval (1/τ) on the frequency axis of frequency space, are related by a Fourier transformation.

In general, in imaging where a radiofrequency burst pulse is applied, the principle is used where an impulse having a fixed interval on the time axis is a spectra having a fixed interval on the frequency axis. If we consider the series of impulses (δ function series 1) on the time axis shown in FIG. 23 as sub-pulses of a radiofrequency burst pulse, and a spectrum on the frequency axis (δ function series 2) is an area where nuclear magnetization is excited, the correspondence relationship between the radiofrequency burst pulse and the excitation area can easily be understood.

To assign tags with less blurring of bright spots due to recovery of suppressed nuclear magnetization from the end of the tagging sequence to the start of the imaging sequence, it is desirable to completely suppress the nuclear magnetization of the area excepting the bright spots. The shape of the excitation area depends on the shape of the sub-pulses, and sub-pulses which make the shape of the excitation are a rectangular may be used.

FIG. 24 is a diagram describing the relation of the amplitude modulated burst pulse shown in FIG. 22 in real space and frequency space, and the correspondence relation between excitation frequency and the excitation area when an amplitude modulated burst pulse using two excitation frequencies is applied. By a Fourier transformation, the amplitude modulated burst pulse in real space shown in FIG. 22 becomes the rectangular periodic wave 1 having a specific width (½(2τ)) on the frequency axis of the frequency space. The rectangular parts above the frequency axis of the waveform of the rectangular periodic wave 1 (comb-shaped area where rectangular parts for which the value on the vertical axis is not 0 are like the teeth of a comb) are areas excited by the amplitude modulated burst pulse.

If the relation between the time interval of the sub-pulses and the period T of the sinc function is T=2τ, the areas which are excited and the areas which are not excited appear alternately with the same volume. On the frequency axis of the frequency space, the area where nuclear magnetization is excited is a rectangular periodic wave having a specific width, so in the tagging sequence using an amplitude modulated burst pulse, an ideal modulation of nuclear magnetization for assigning tags with less blurring of bright spots can be performed.

If the carrier frequency of the amplitude modulated burst pulse is shifted by 1/(2τ) Hz, it becomes a rectangular periodic wave 2 wherein the rectangular periodic wave 1 is shifted by 1/(2τ) Hz on the frequency axis. As a result, areas where the waveform of the rectangular periodic wave 1 is excited, are areas where the waveform of the rectangular periodic wave 2 is not excited, and areas where the waveform of the rectangular periodic wave 1 is not excited, are areas where the waveform of the rectangular periodic wave 2 is excited. In other words, the areas which are excited and the areas which are not excited are reversed in the rectangular periodic wave 1 and the rectangular periodic wave 2. Due to the irradiation of the subject to be inspected with these amplitude modulated burst pulses, the nuclear magnetization in the imaging cross-section of the subject to be inspected is substantially uniform.

Next, the imaging time required until measurement of the echo signal needed for image reconstruction is completed, and the imaging sequence, will be described. The imaging times due to the pulse sequences in FIG. 25A and FIG. 25B will be compared. If the data amount (e.g., number of sampling points acquired from one echo signal) is equal, the imaging times may be compared as indicators of the echo acquisition efficiency.

In FIG. 25A and FIG. 25B, the application times of the π pulse, slice gradient magnetic field Gs and phase encoded gradient magnetic field Gp are identical. Therefore, the application time of the readout gradient magnetic field Gr and the number of echo signals generated during application of the readout gradient magnetic field Gr are the main factors in determining the echo acquisition efficiency.

In the pulse sequence of FIG. 25A, plural echo signals are generated corresponding to the number of sub-pulses in the first and second amplitude modulated burst pulses. In the pulse sequence of FIG. 25B, only one echo signal is generated due to application of one π pulse. In the pulse sequence of FIG. 25A, the echo acquisition efficiency is several times that of the pulse sequence of FIG. 25B. Therefore, in the pulse sequence of FIG. 25A, the time for which the subject must be restricted to draw the heart can be shortened to a fraction compared to the pulse sequence of FIG. 25B. As the effect of movement of the subject is less, the reliability of the data is improved.

As described above, an amplitude modulated burst pulse is used in the tagging sequence and imaging sequence, so fast imaging can be performed, and higher precision of extracting cardiac functions is realized.

According to this invention, tags are assigned by applying an amplitude modulated burst pulse. This permits a large reduction in blurring of the bright spots of the tags, a large reduction in the time for which the subject must be restrained to acquire an image, fast imaging of the heart, and improved precision in extracting cardiac function.

The method of nuclear magnetic resonance imaging according to this invention has the following features.

First construction: (1) a step which detects a periodic physiological signal, (2) a step which generates a synchronizing signal which initiates a pulse sequence which detects, from the physiological signal, a nuclear magnetic resonance signal from a subject to be inspected, and (3) a step which synchronizes a first radiofrequency burst pulse comprising plural sub-pulses formed at equidistant intervals on the time axis whereof the amplitudes are modulated by a sinc function and a gradient magnetic field in a first or second direction with the synchronizing signal, applies them, and modulates the nuclear magnetization of the subject to be inspected in the first or second direction.

Second construction: (1) a step which detects a periodic physiological signal, (2) a step which generates a synchronizing signal which initiates a pulse sequence which detects, from the physiological signal, a nuclear magnetic resonance signal from a subject to be inspected, (3) a step which synchronizes a first radiofrequency burst pulse comprising plural sub-pulses formed at equidistant intervals on the time axis whereof the amplitudes are modulated by a sinc function and a gradient magnetic field in a first or second direction with the synchronizing signal, applies them, and modulates the nuclear magnetization of the subject to be inspected in the first direction, and (4) a step which applies a second radiofrequency burst pulse comprising plural sub-pulses formed at equidistant intervals on the time axis whereof the amplitudes are modulated by a sinc function, and a gradient magnetic field, and modulates the nuclear magnetization of the subject to be inspected in the second direction.

Third construction: (1) a step which detects a periodic physiological signal, (2) a step which generates a synchronizing signal which initiates a pulse sequence which detects, from the physiological signal, a nuclear magnetic resonance signal, (3) a step which synchronizes a first radiofrequency burst pulse comprising plural sub-pulses formed at equidistant intervals on the time axis whereof the amplitudes are modulated by a sinc function and a gradient magnetic field in a first or second direction with the synchronizing signal, applies them, and modulates the nuclear magnetization of the subject to be inspected in the first or second direction, (4) applies the second radiofrequency burst pulse comprising plural sub-pulses formed at equidistant intervals on the time axis whereof the amplitudes are modulated by a sinc function and the gradient magnetic field in the first direction to excite the nuclear magnetization of the subject to be inspected after a predetermined waiting time has elapsed following implementation of the step (3), (5) applies a radiofrequency magnetic field pulse while a gradient magnetic field is applied in the third direction, (6) assigns positional information in the second direction to the nuclear magnetization due to application of the gradient magnetic field in the second direction, generates a nuclear magnetic resonance signal in which positional information in the first direction is assigned to the nuclear magnetization due to application of the gradient magnetic field in the first direction, and measures the nuclear magnetic resonance signal, (7) repeats the steps (5) and (6) plural times, and (8) repeats the steps from (1) to (7) plural times.

Fourth construction: (1) a step which detects a periodic physiological signal, (2) a step which generates a synchronizing signal which initiates a pulse sequence which detects, from the physiological signal, a nuclear magnetic resonance signal, (3) a step which synchronizes a first radiofrequency burst pulse comprising plural sub-pulses formed at equidistant intervals on the time axis whereof the amplitudes are modulated by a sinc function and a gradient magnetic field in a first direction with the synchronizing signal, applies them, and modulates the nuclear magnetization of the subject to be inspected in the first direction, (4) applies the second radiofrequency burst pulse comprising plural sub-pulses formed at equidistant intervals on the time axis whereof the amplitudes are modulated by a sinc function and the gradient magnetic field in the second direction to modulate the nuclear magnetization of the subject to be inspected in the second direction, (5) applies a third radiofrequency burst pulse comprising plural sub-pulses formed at equidistant intervals on the time axis whereof the amplitudes are modulated by a sinc function and the gradient magnetic field in the first direction to excite the nuclear magnetization of the subject to be inspected after a predetermined waiting time has elapsed following implementation of the step (4), (6) applies a radiofrequency magnetic field pulse while a gradient magnetic field is applied in the third direction, (7) assigns positional information in the second direction to the nuclear magnetization due to application of the gradient magnetic field in the second direction, generates a nuclear magnetic resonance signal in which positional information in the first direction is assigned to the nuclear magnetization due to application of the gradient magnetic field in the first direction, and measures the nuclear magnetic resonance signal, (8) repeats the steps (6) and (7) plural times, and (9) repeats the steps from (1) to (8) plural times.

DESCRIPTION OF THE PREFERRED EMBODIMENTS

Hereafter, some embodiments of this invention will be described in detail referring to the appended drawings. In FIG. 1 to FIG. 25, RF is a radiofrequency magnetic field pulse, Gr is a readout gradient magnetic field, Gp is a phase encoded gradient magnetic field, Gs is a slice gradient magnetic field, Echo is an echo signal, and A/D is A/D conversion of the echo signal (measurement of the echo signal). The readout gradient magnetic field, phase encoded gradient magnetic field and slice gradient magnetic field are applied in one of the x, y and z directions.

Figure 21:
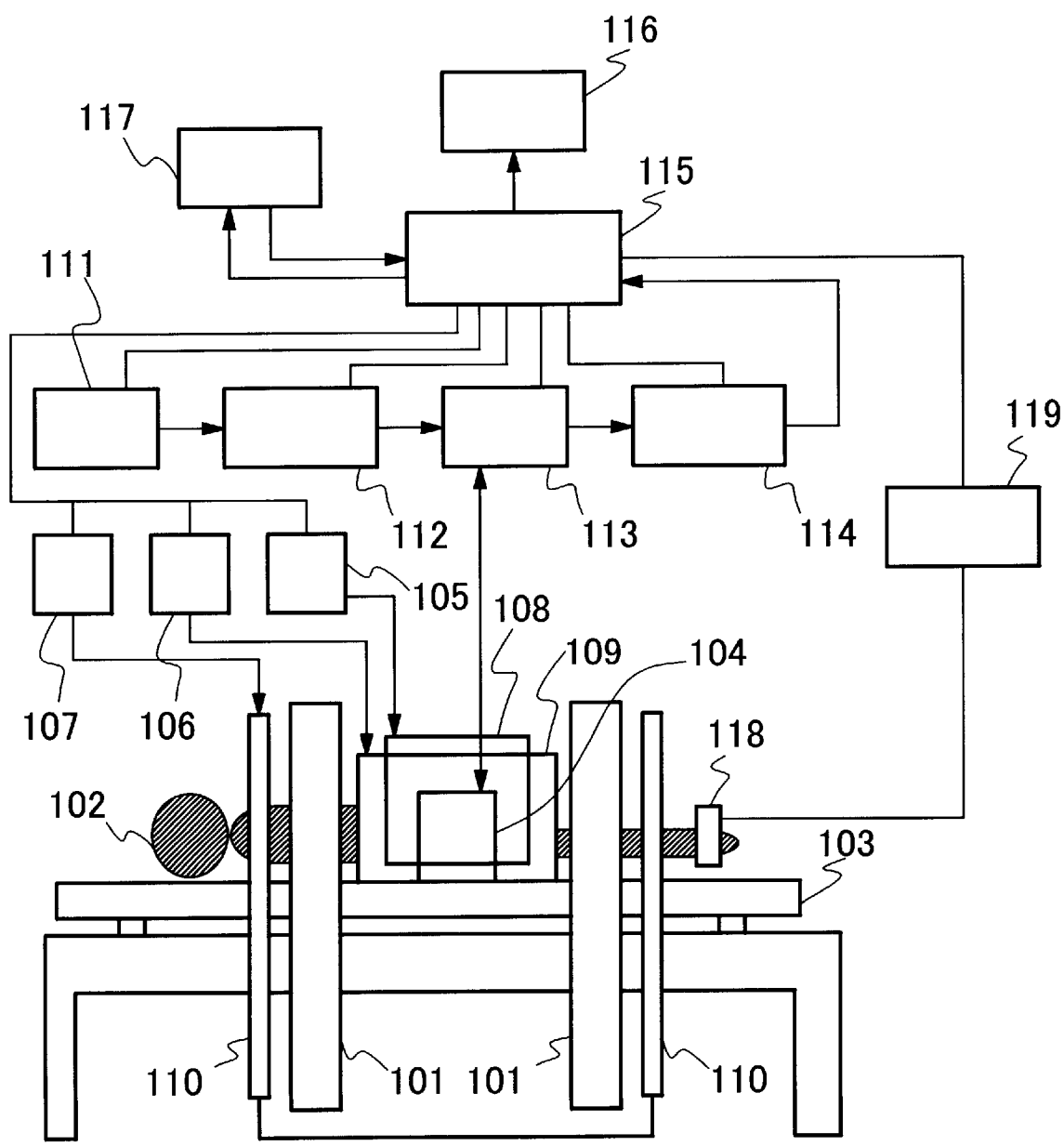
FIG. 21 is a diagram describing the construction of an MRI apparatus to which this invention is applied.
Figure 22:
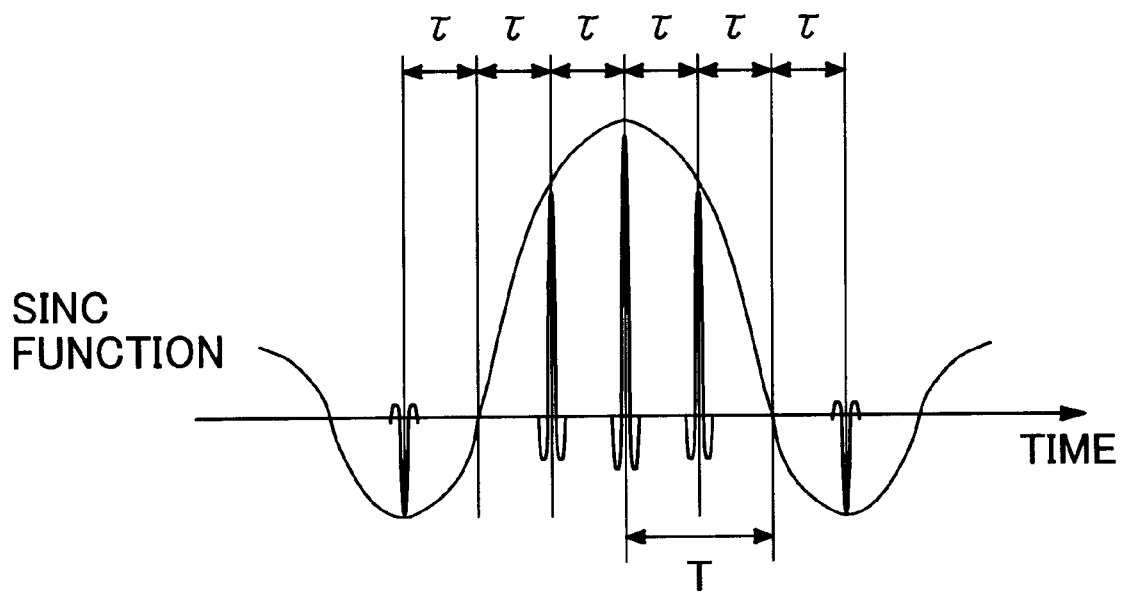
FIG. 22 is a diagram describing an amplitude modulated burst pulse according to the prior art.
Figure 23:
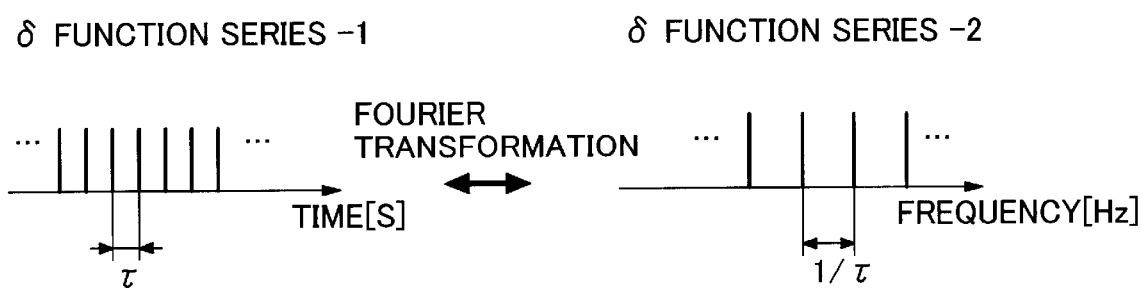
FIG. 23 is a diagram describing the relation of a series of impulses in real space and frequency space (prior art).

FIG. 21 is a diagram describing the construction of an MRI apparatus to which this invention is applied. A subject 102 to be inspected lying on a bed 103 is placed in the space of a static magnetic field 101 generated by a static magnetic field generating coil or a magnet 101. A radiofrequency magnetic field generated by a radiofrequency magnetic field generating coil 104 and a gradient magnetic field generated by gradient magnetic field generating coils 108, 109, 110, are applied to the subject 102 to be inspected according to a predetermined pulse sequence controlled by a control means 119. Currents are respectively supplied by coil driving units 105, 106, 107 to the gradient magnetic field generating coils 108, 109, 110 which generate gradient magnetic fields in the x direction, y direction and z direction.

The nuclear magnetic resonance signal (echo signal) produced from the subject 102 to be inspected is detected by the radiofrequency magnetic field generating coil 104. The a detected echo signal is acquired by a computer 115 and subjected to signal processing, and an image reconstruction computation is performed. The reconstructed image obtained by the image reconstruction computation is displayed on a CRT display 116. The signal processing results, data obtained during the image reconstruction computation and the reconstructed image are stored in a memory 117. When the imaging is performed in synchronism with the heartbeat or respiration, a physiological signal detecting means 118 such as an electrocardiograph is fitted to the subject 102 to be inspected.

In FIG. 21, the arrows show the procedure used for processing of nuclear magnetic resonance signals, and the flow of current output related to generation of magnetic fields. The solid lines show the interconnections of the main control signals sent and received. The driving of the radiofrequency magnetic field, driving of the gradient magnetic field and detection of physiological signals are performed by the output of control signals from the control means 119. In the example shown in FIG.21, the computer 115 receives control signals from the control means 119 to control the above operations, but the computer 115 may be combined with the control means 119.

The wave form of a radiofrequency generated by a synthesizer 111 is shaped by a modulating unit 112 and power-amplified by an amplifier 113, and the resulting current is supplied to the radiofrequency magnetic field generating coil 104. The radiofrequency magnetic field output by the radiofrequency magnetic field generating coil 104 is irradiated to the subject 102 to be inspected, and the nuclear magnetization of the subject 102 to be inspected is thereby excited. The echo signal generated from the subject 102 to be inspected is received by the radiofrequency magnetic field generating coil 104, amplified by the amplifier 113, detected by a wave detecting apparatus 114, input to the computer 115 and stored in the memory 117. The computer 115 performs an image reconstruction computation, and the reconstructed image obtained is displayed on the CRT display 116.

When the imaging is performed in synchronism with the heartbeat, the physiological signal output by the physiological signal detecting means 118 is input to the control means 119. The control means 119 detects the R wave of an electrocardiogram and generates a synchronizing signal, and after a predetermined waiting time, control of a predetermined pulse sequence is performed.

Figure 1:
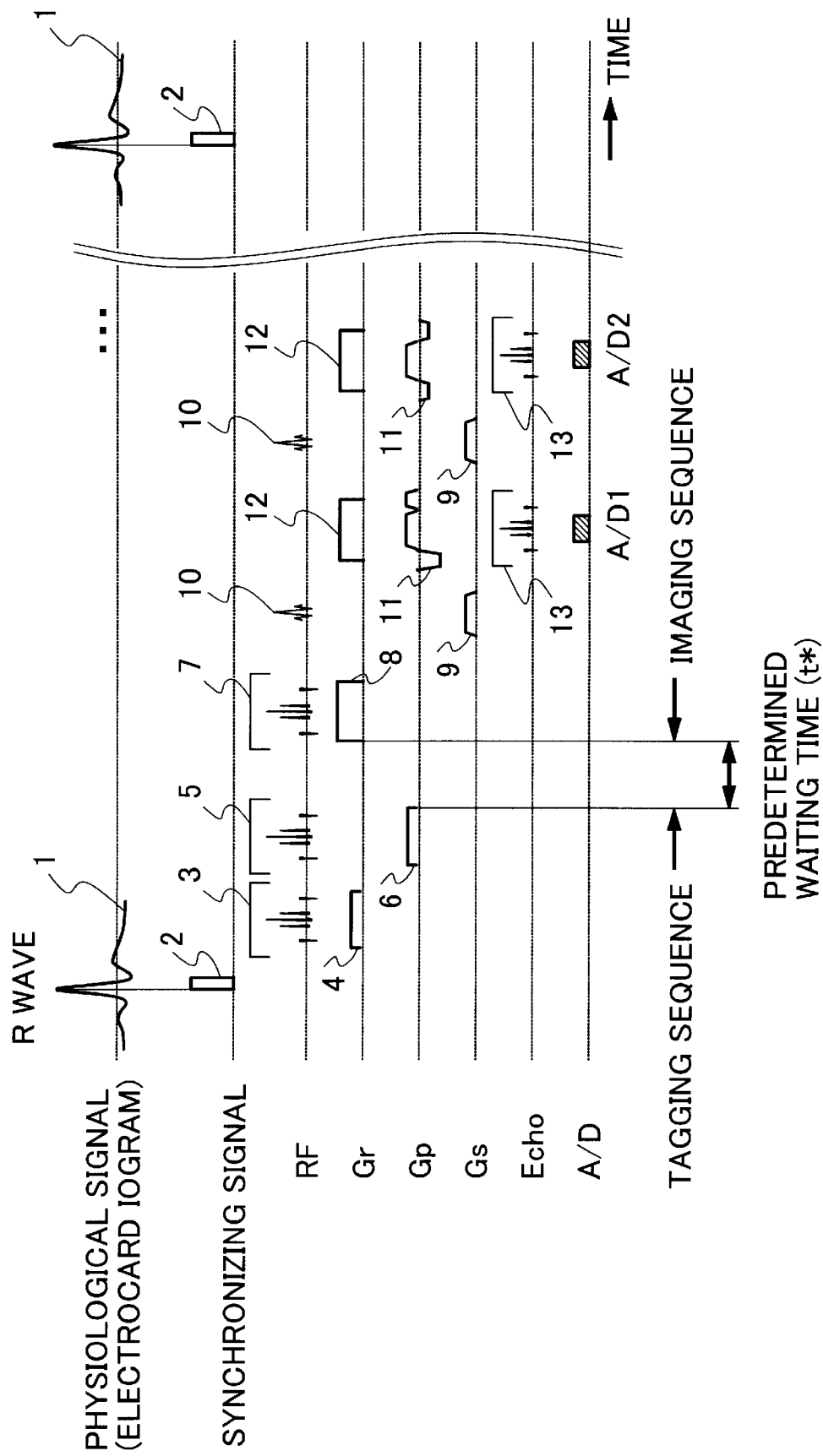
FIG. 1 is a diagram describing a pulse sequence in an embodiment according to this invention, wherein imaging is performed by assigning tags in two directions.

FIG. 1, which shows one embodiment of this invention, is a diagram describing a pulse sequence wherein an amplitude modulated burst pulse is used for the tagging sequence and imaging sequence, and imaging is performed by assigning tags in two directions.

In the pulse sequence shown in FIG. 1, the physiological signal is first detected to generate the synchronizing signal. An electrocardiogram 1 which is a typical physiological signal is detected by the physiological signal detecting means 118, and input to the control means 119. The control means 119 detects the R wave from the waveform of the input electrocardiogram, and outputs a synchronizing signal 2. The computer 115 receives a control signal from the control means 119, and controls the driving of the radiofrequency magnetic field, driving of the gradient magnetic field and detection of the physiological signal by the control signal from the control means 119.

A first radiofrequency burst pulse (amplitude modulated burst pulse) 3 comprising plural sub-pulses formed at equidistant intervals on the time axis whereof the amplitudes are modulated by a sinc function, and a gradient magnetic field Gr4 in a first direction (readout direction) are synchronized with the synchronizing signal 2, applied, and the nuclear magnetization of the subject to be inspected is modulated in the first direction. Subsequently, a second radiofrequency burst pulse (amplitude modulated burst pulse) 5 comprising plural sub-pulses formed at equidistant intervals on the time axis whereof the amplitudes are modulated by a sinc function, and a gradient magnetic field Gp6 in a second direction (phase encoding direction) are applied, and the nuclear magnetization of the subject to be inspected is modulated in the second direction. As a result, the nuclear magnetization of the subject to be inspected is modulated in two directions (readout direction and phase encoding direction), and tags are assigned (tagging sequence).

Figure 20:
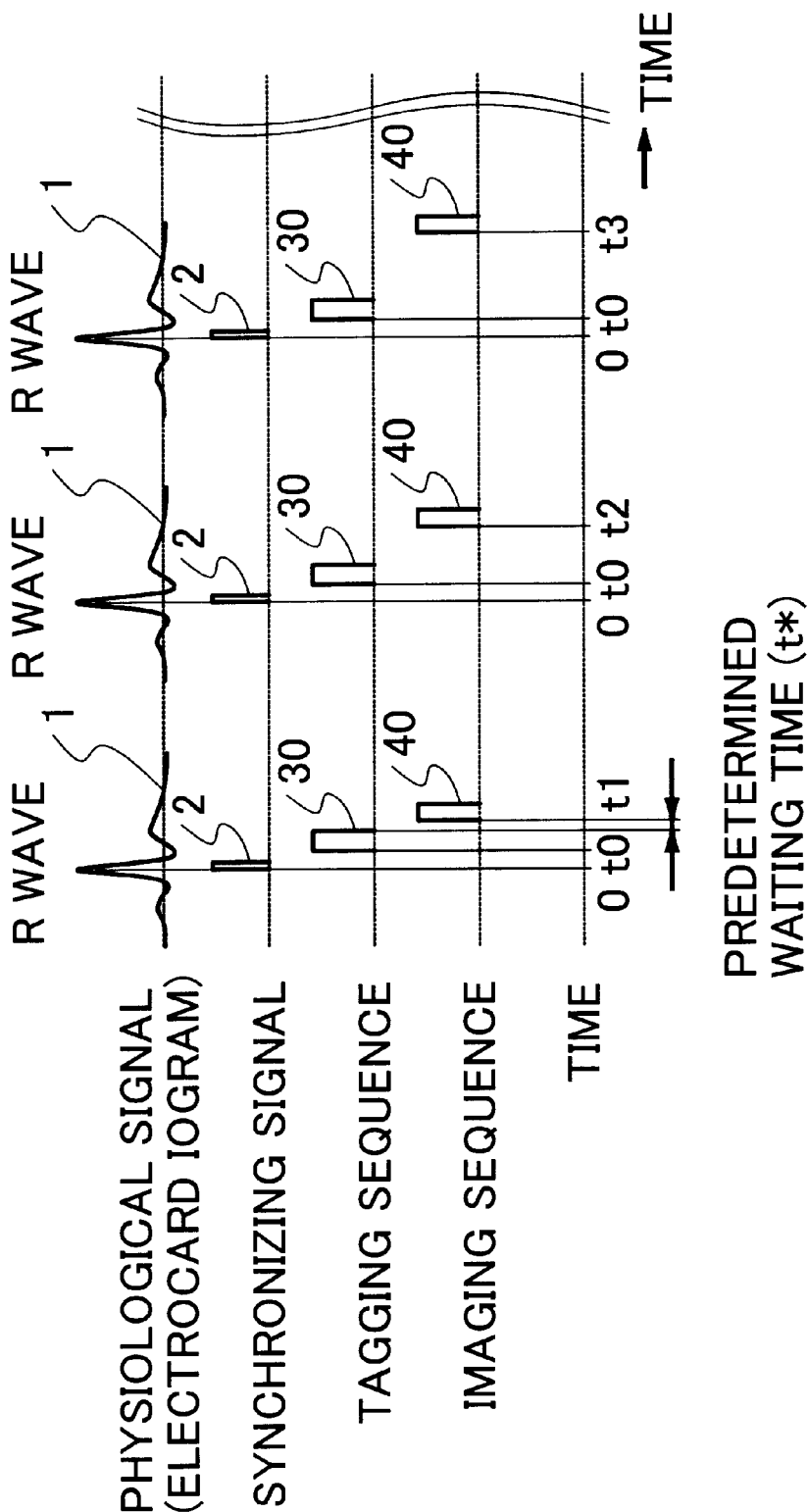
FIG. 20 is a diagram describing a pulse sequence in an MRI apparatus according to the prior art which performs tagging and images the movement of the heart.

The time from the synchronizing signal 2 to application of the first radiofrequency burst pulse 3 (the aforesaid predetermined waiting time) is generally from several msec to several 10 msec, and as in the case of the example of FIG. 20, it is not modified in the tagging sequence implemented before the imaging sequence of the periods of the cardiac cycle.

After a predetermined waiting time t*has elapsed from completion of the tagging sequence, a third radiofrequency burst pulse (amplitude modulated burst pulse) 7 comprising plural sub-pulses formed at equidistant intervals on the time axis whereof the amplitudes are modulated by a sinc function, and a gradient magnetic field Gr8 in the first direction (readout direction) are applied, and the nuclear magnetization of the subject to be inspected is excited. Subsequently, an imaging slice plane is selected by applying a gradient magnetic field Gs9 and radiofrequency magnetic field pulse 10 in a third direction (slice direction) orthogonal respectively to the first direction (readout direction) and second direction (phase encoding direction), and the nuclear magnetization is simultaneously inverted.

Next, positional information in the second direction is assigned to the nuclear magnetization by applying a gradient magnetic field Gp11 in the second direction (phase encoding direction). Likewise, positional information in the first direction is assigned to the nuclear magnetization by applying a gradient magnetic field Gp12 in the first direction (readout direction), generating an echo signal 13, and measuring the echo signal. Subsequently, the sequence of steps from applying the gradient magnetic field in the third direction and the radiofrequency magnetic field is repeated, and data necessary for reconstruction of the MRI image are obtained (imaging sequence).

In the procedure described above, in a predetermined period of the cardiac cycle given by the time from generation of the synchronizing signal to applying the third radiofrequency burst pulse 7 and gradient magnetic field Gr8 in the first direction, the MRI image of the heart to which tags are assigned can be acquired in a short time.

Further, by repeating the sequence of steps from detecting the physiological signal to completing the measurement of the echo signal required to reconstruct the MRI image with modification of the waiting time t*, an MRI image to which tags are assigned can be acquired in different periods of the cardiac cycle, and cardiac functions can be extracted to high precision. In the example shown in FIG. 1, the nuclear magnetization was modulated in the order of the readout direction and phase encoding direction, but the reverse order is also possible.

Figure 2:
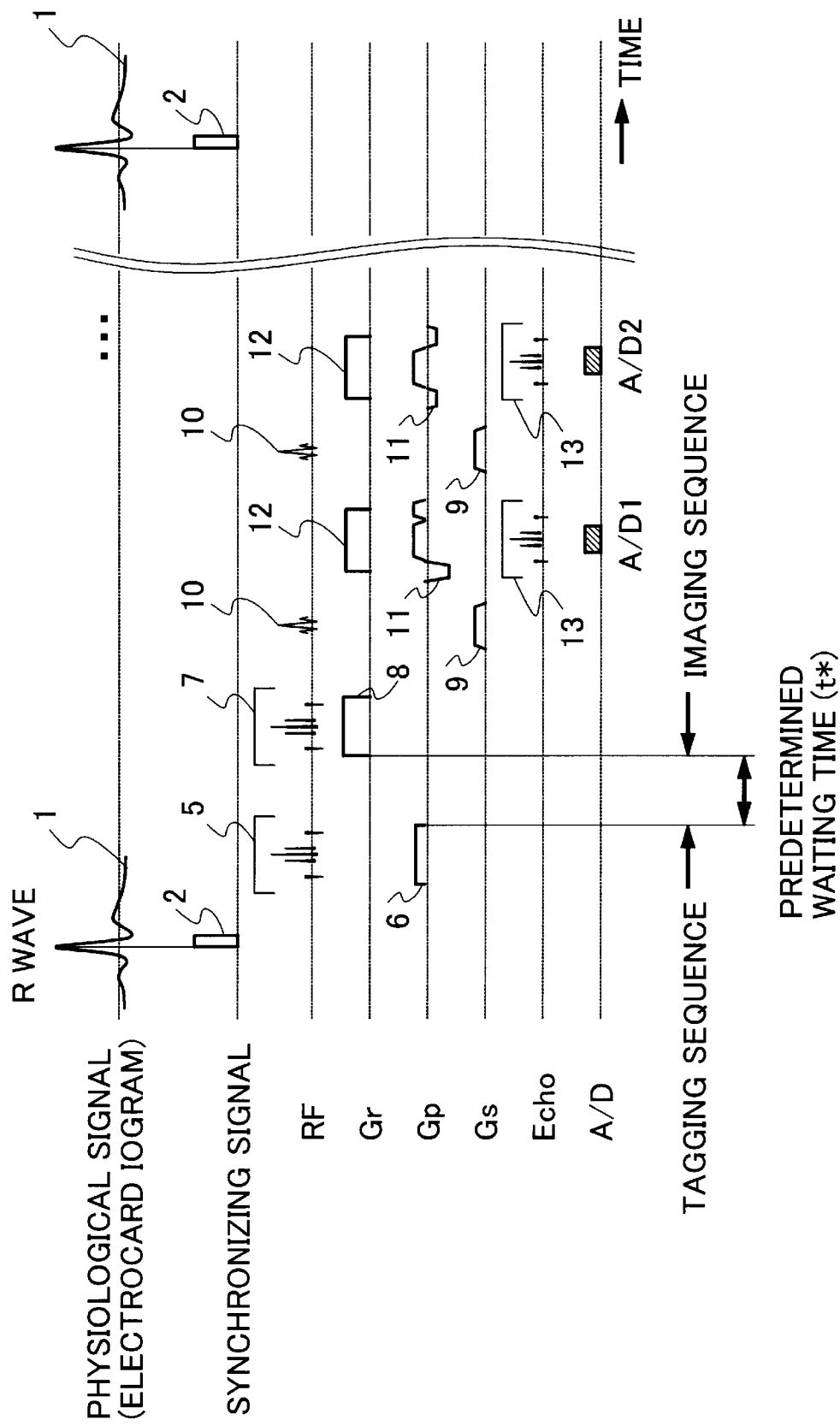
FIG. 2 is a diagram describing a pulse sequence in an embodiment according to this invention, wherein imaging is performed by assigning tags in one direction.

FIG. 2 is a diagram showing an embodiment of this invention describing a pulse sequence wherein an amplitude modulated burst pulse is used for the tagging sequence and imaging sequence, and imaging is performed by assigning tags in only one direction. The nuclear magnetization is modified in only one of the first direction (readout direction) and second direction (phase encoding direction), and tags are assigned in only one direction.

In the example shown in FIG. 2, tags are assigned in only the second direction (the phase encoding direction). Assigning tags in only one direction is effective when the functional information it is desired to obtain (e.g., displacement amount or speed of motion) can be represented in one dimension. The imaging sequence in FIG. 2 is identical to the imaging sequence shown in FIG. 1.

Figure 3:
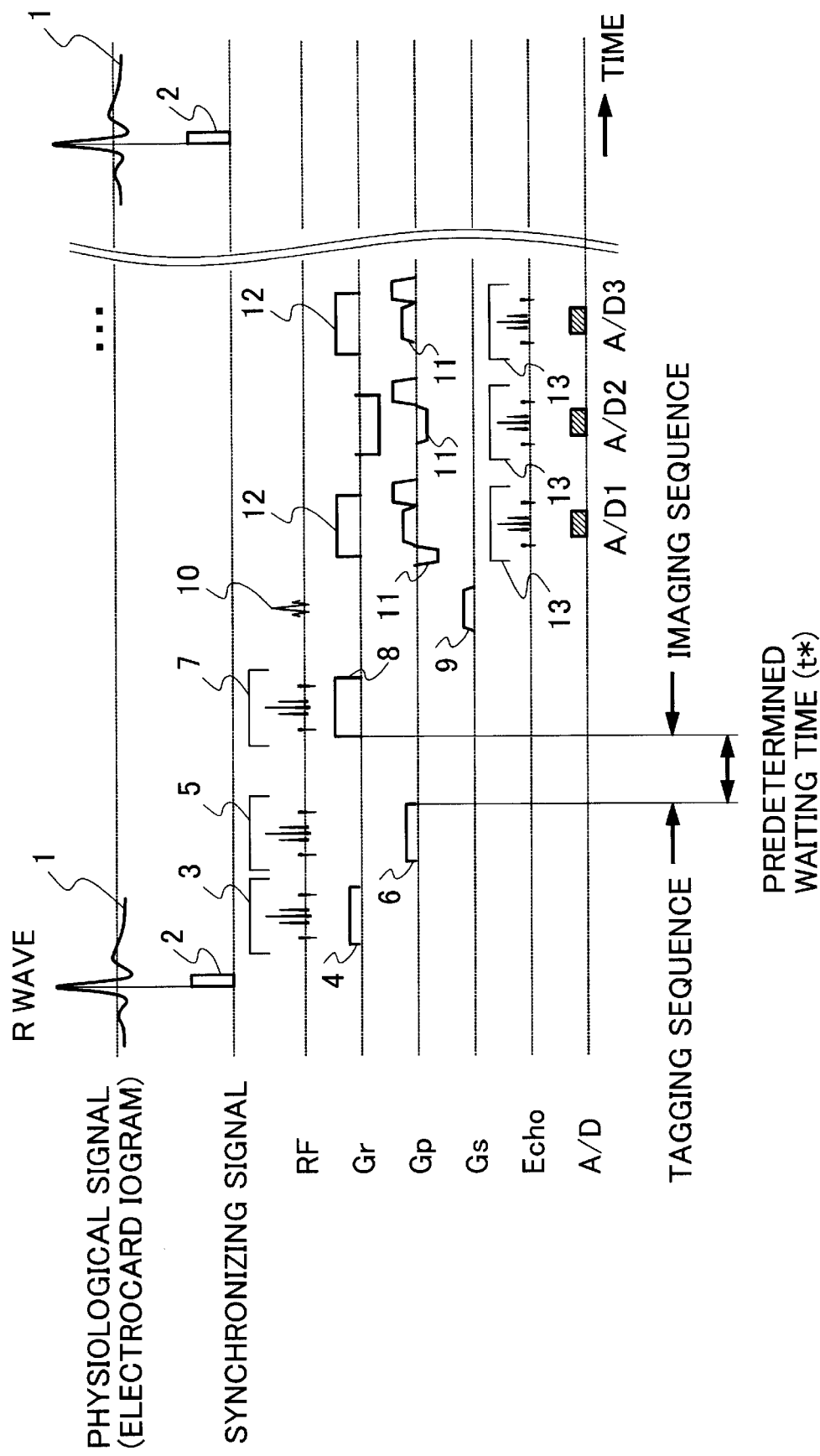
FIGS. 3, 4 and 5 are diagrams describing pulse sequences in an embodiment according to this invention, wherein imaging is performed by assigning tags in two directions.

FIG. 3 is a diagram showing an embodiment of this invention describing a pulse sequence wherein an amplitude modulated burst pulse is used for the tagging sequence and imaging sequence, and imaging is performed by assigning tags in two directions. In the example shown in FIG. 1, the nuclear magnetization was inverted by applying a radiofrequency magnetic field pulse to generate an echo signal, but in FIG. 2, a pulse sequence which generates an echo signal by inverting the polarity of a readout gradient magnetic field Gr12, is used as the imaging sequence.

The tagging sequence and imaging sequence can be selected independently, so a pulse sequence according to the prior art can also be used as either of the pulse sequences.

Figure 4:
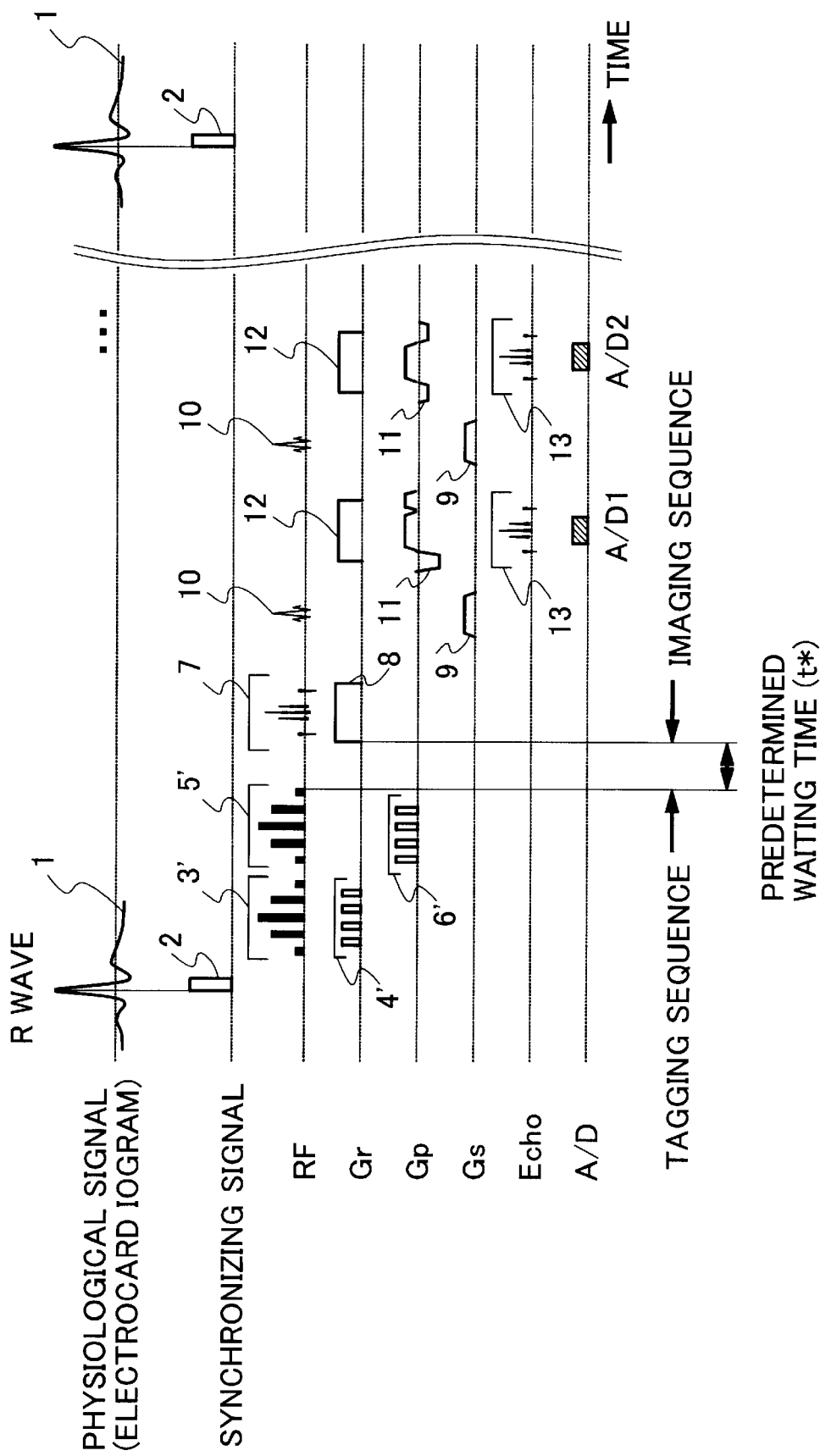

FIG. 4 is a diagram showing an embodiment of this invention describing a pulse sequence wherein an amplitude modulated burst pulse is used for the imaging sequence, a pulse sequence according to a prior art technique shown in FIG. 9 is used for the tagging sequence, and imaging is performed by assigning tags in two directions. The imaging sequence in FIG. 4 is identical to the imaging sequence shown in FIG. 1. In the pulse sequence shown in FIG. 4, the imaging time can be shortened.

Figure 5:
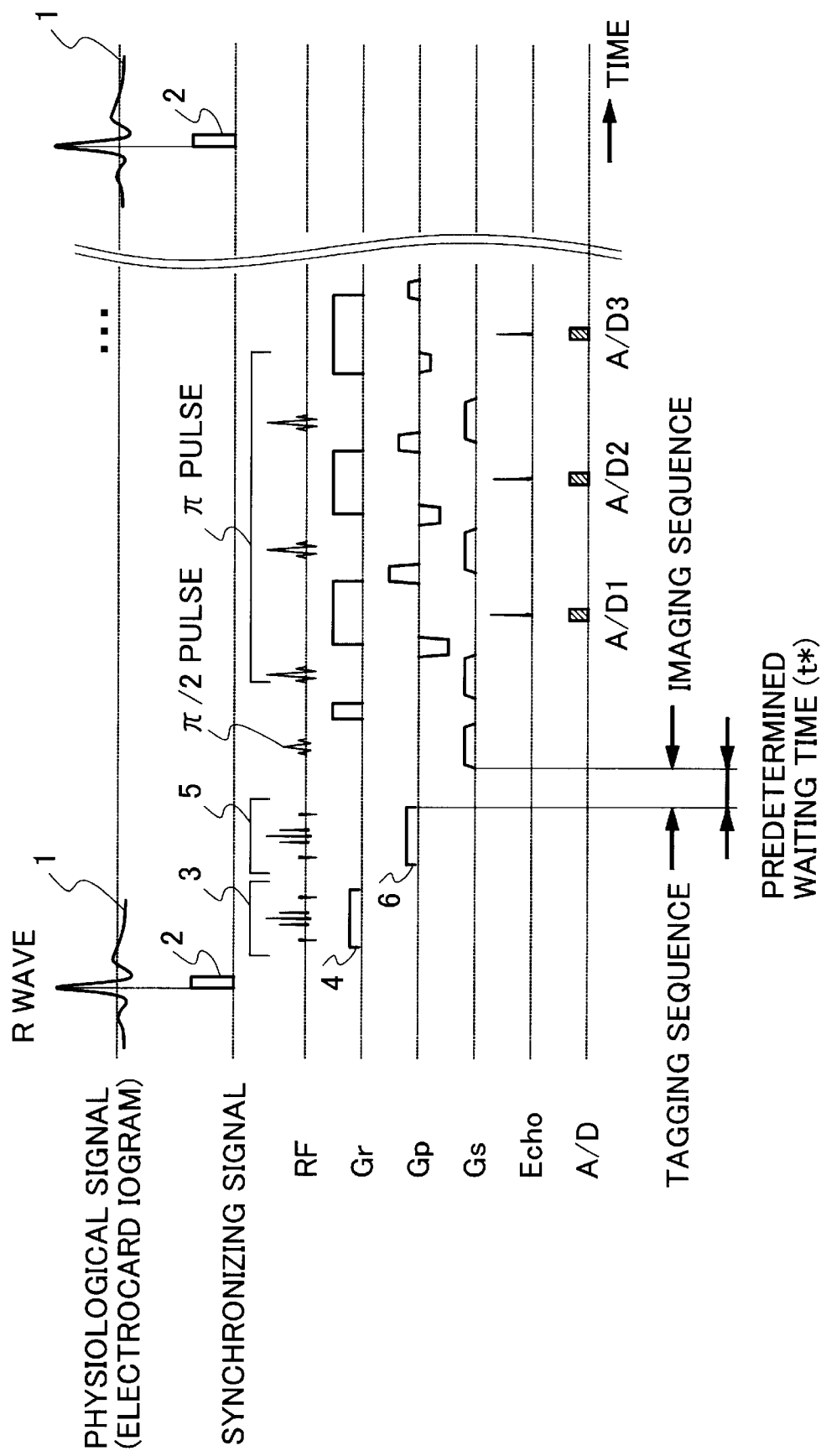
Figure 25A:
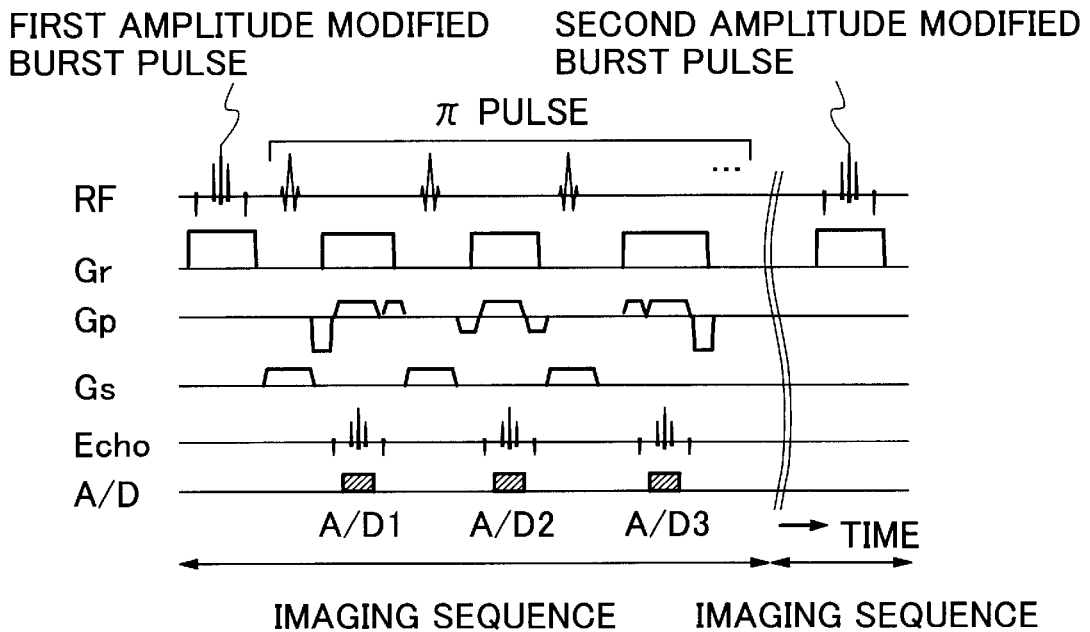
FIGS. 25A, 25B are diagrams describing an imaging sequence according to the prior art.
Figure 25B:
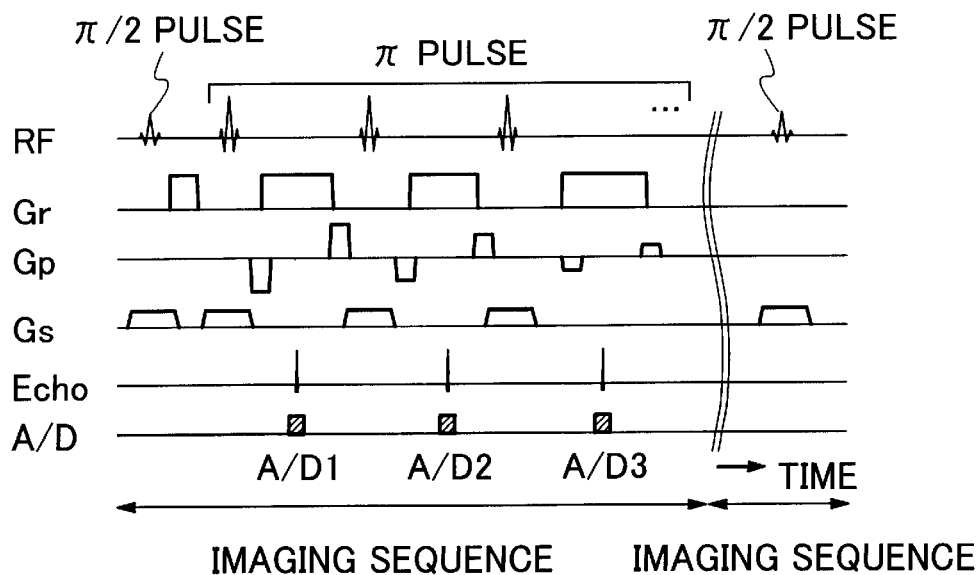

FIG. 5 is a diagram showing an embodiment of this invention describing a pulse sequence wherein an amplitude modulated burst pulse is used for the tagging sequence, a pulse sequence according to a fast spin echo method shown in FIG. 25B is used for the imaging sequence, and imaging is performed by assigning tags in two directions. In the pulse sequence shown in FIG. 5, blurring of the bright spots of the tags can be reduced.

In the imaging sequence shown in FIG. 1 to FIG. 4, echo signal measurement by applying the amplitude modulated burst pulse 7 is shown, but this is a series of imaging sequences including also echo signal measurements by applying amplitude modulated burst pulses wherein the carrier frequency of the amplitude modulated burst pulse 7 is shifted (not shown in the imaging sequences shown in FIG. 1 to FIG. 4). Specifically, the nuclear magnetization in the imaging cross-section of the subject to be inspected can be excited essentially uniformly, and the echo signal due to nuclear magnetization in the imaging cross-section can be measured by a series of imaging sequences comprising application of the amplitude modulated burst pulse 7, and application of amplitude modulated burst pulses wherein the carrier frequency of the amplitude modulated burst pulse 7 is shifted, as in the case of the pulse sequence shown in FIG. 25.

As described above, the blurring of tags can be reduced and an MRI image of the heart can be acquired in a short time by using an amplitude modulated burst pulse for at least one of the tagging sequence and imaging sequence.

In the examples of the imaging sequences shown in FIG. 1 to FIG. 4, the case was described where the echo signal was measured by exciting the nuclear magnetization in the imaging cross-section of the subject by amplitude modulated burst pulses having two different excitation frequencies, by applying the amplitude modulated burst pulse 7, and amplitude modulated burst pulses wherein the carrier frequency of the amplitude modulated burst pulse 7 is shifted. However, this is not limiting, and the echo signal may also be measured by exciting the nuclear magnetization of the subject to be measured by amplitude modulated burst pulses of a larger number of excitation frequencies than two, by varying the shift amount of the carrier frequency in m ways (m=number of exponentiations of 2).

Figure 19:
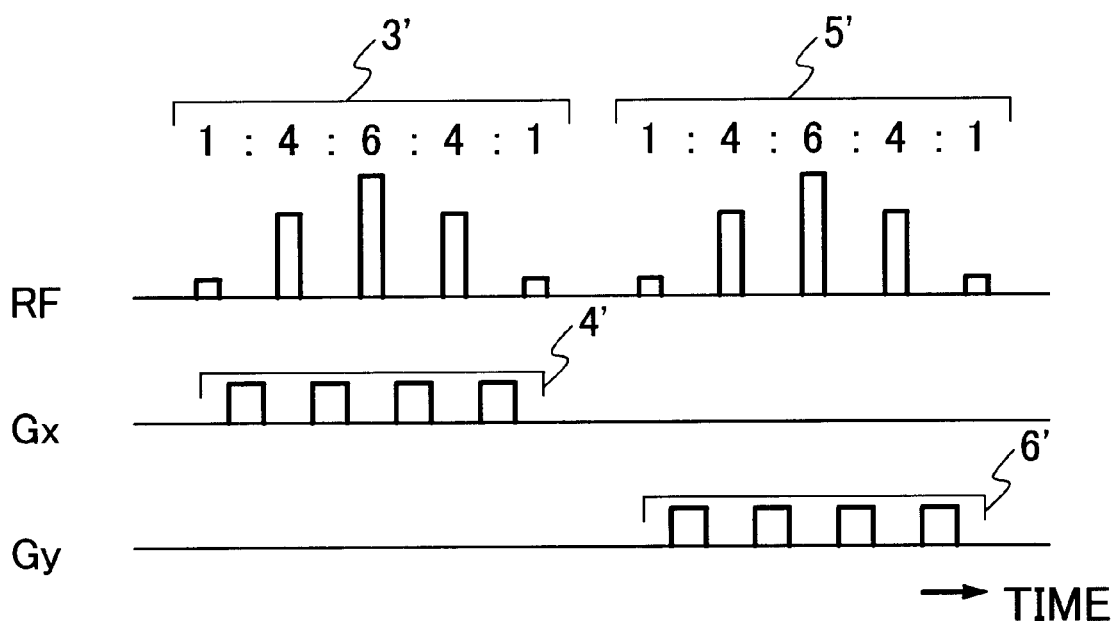
FIG. 19 is a diagram describing a tagging sequence according to the prior art.

The tagging method of the prior art shown in FIG. 19 and the tagging method of this invention using amplitude burst pulses, may be combined. For example, tags may be assigned in one direction by applying an amplitude modulated burst pulse and a gradient magnetic field as shown in FIG. 2, a binomial SPAMM (Spatial Modulation of Magnetization) pulse may be used as the radiofrequency magnetic field pulse, tags may be assigned in the second direction by applying this radiofrequency magnetic field pulse and gradient magnetic field, as shown in FIG. 19, and the nuclear magnetization modulated in two directions.

Assuming the pulse sequence shown in FIG. 1 to FIG. 5 is the same as the pulse sequence in the prior art shown in FIG. 20, the tagging sequence 30 is executed at the time t0 immediately after the synchronizing signal 2 is detected from the R wave of the electrocardiogram, the echo signal is measured modifying only the starting time of the imaging sequence 40, i.e., t1, t2, t3 . . . , and MRI images 1, 2, 3 are acquired. The amount of movement of the heart wall and the speed of motion of the heart wall which are parameters of cardiac function can be extracted by comparing the positions of bright points of the tags between the MRI images 1, 2, 3.

Following the tagging sequence performed at the time t0 immediately after the synchronizing signal detected from the R wave of the electrocardiogram, the MRI images 1, 2, 3 may be obtained based on the added values of echo signals measured by implementing the imaging sequence and modifying the starting times (t1, t2, t3 . . . ). When the MRI images are obtained based on added values of the echo signal, an image of high S/N is obtained, and precise parameters for evaluating cardiac function can be found.

Figure 6:
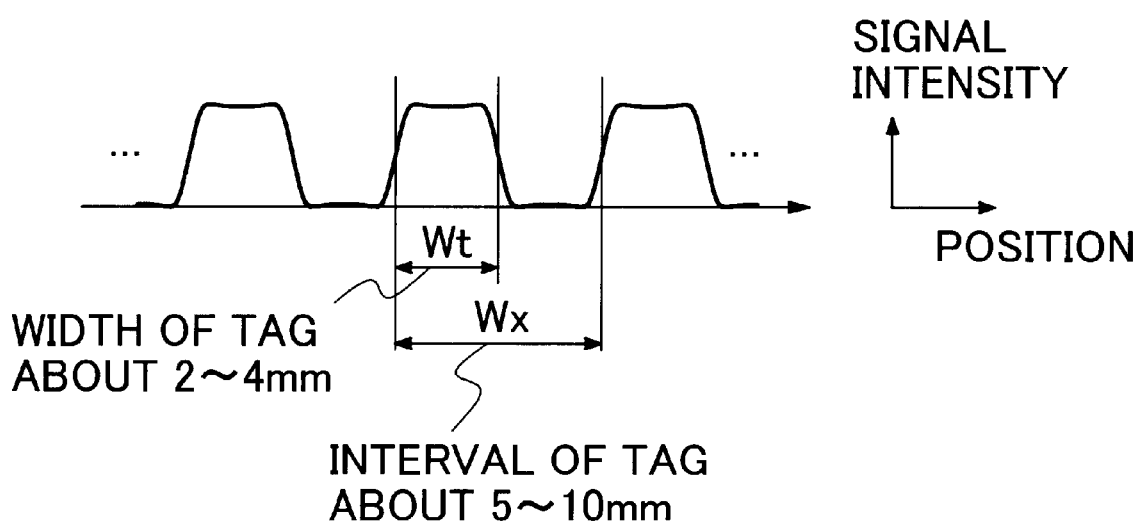
FIG. 6 is a diagram describing the width of tags and interval between tags in an embodiment according to this invention.

FIG. 6 is a diagram describing a width Wt of the tags and an interval Wx of the tags in an embodiment of this invention. As shown in FIG. 6, in general, Wt is of the order of 2 mm–4 mm, and Wx is of the order of 5 mm–10 mm. Therefore, when tags are assigned, the parameters of the pulse sequence when the amplitude modulated burst pulse is applied are adjusted so that the width of the excitation area shown in FIG. 6 (comb-shaped area wherein rectangular parts where the signal intensity is not 0 are the teeth of the comb) is approximately 2 mm–4 mm. In other words, in the tagging sequence, the nuclear magnetization is excited in a rectangular periodic region of width Wt and interval Wx.

On the other hand, in the case of imaging, a spatial resolution of the order of 1 mm is required. Therefore, the parameters of the pulse sequence comprising application of the amplitude modulated burst pulse are adjusted so that the width of the excitation area is approximately 1 mm.

Hereafter, the relation between the width Wt of the tagged area and the pixel size Wi of the MRI image, and adjustment of the parameters of the pulse sequence, will be described.

FIG. 7 is an excitation profile due to a tagging sequence which applies an amplitude modulated burst pulse, and an excitation profile due to an imaging sequence, in an embodiment of this invention. The excitation profile is a diagram showing the proportion by which the nuclear magnetization enters an excited state due to application of the amplitude modulated burst pulse (the vertical axis shows the proportion of nuclear magnetization in the excited state, and the horizontal axis shows frequency). In an MRI image, the proportion by which the nuclear magnetization enters the excited state may be correlated with the signal intensity, and the frequency may be correlated with position coordinates, hence in the following description, the vertical axis is represented by signal intensity and horizontal axis is represented by position coordinates in the excitation profile, and the excitation profile is represented by a signal intensity profile. The width of the excitation area is taken as Wt, and the interval between excitation areas is taken as Wx. The pixel size of the MRI image when the image is acquired is taken as Wi.

Figure 7A:
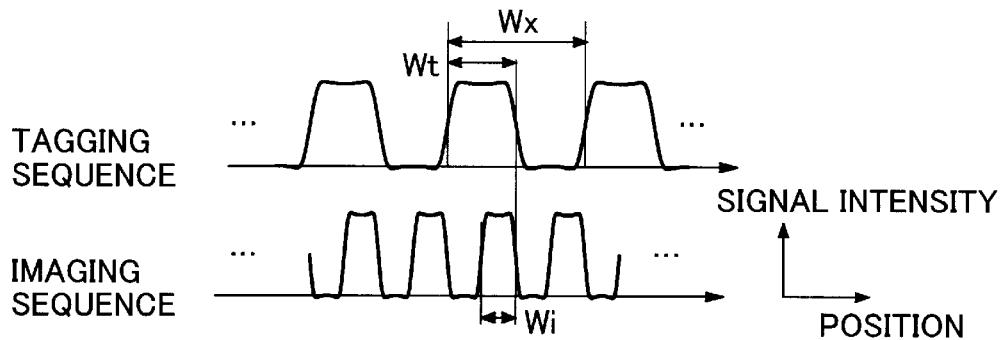
FIGS. 7A, 7B and 7C are diagrams describing an excitation profile in an embodiment according to this invention.
Figure 7B:
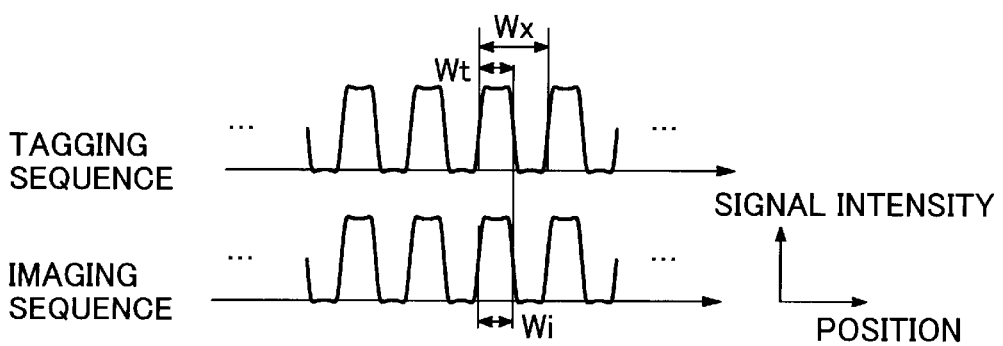
Figure 7C:
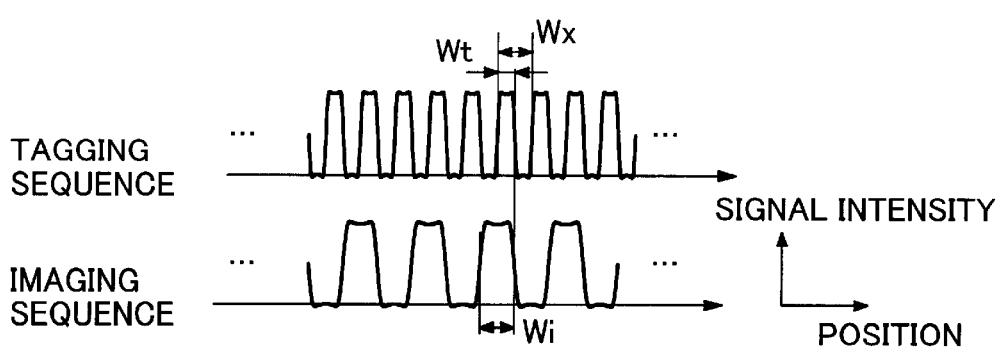

FIG. 7A is a diagram describing the excitation profile due to each sequence when Wt=2×Wi, FIG. 7B is a diagram describing the excitation profile due to each sequence when Wt=Wi, and FIG. 7C is a diagram describing the excitation profile due to each sequence when Wt=Wi/2. The signal intensity profile continuously varies in space, and the pixel size of the MRI image is a finite value. Therefore, the signal intensity profile appears discretized and averaged in the MRI image at the time the echo signal is measured and when the image is reconstructed.

Figure 8A:
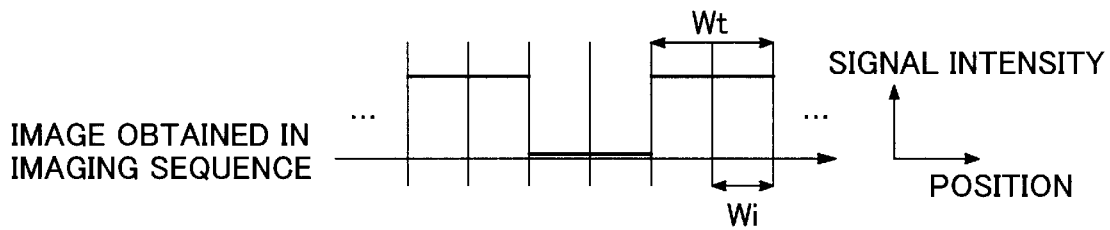
FIGS. 8A, 8B and 8C are diagrams describing a signal intensity profile in an MRI image in an embodiment according to this invention.
Figure 8B:
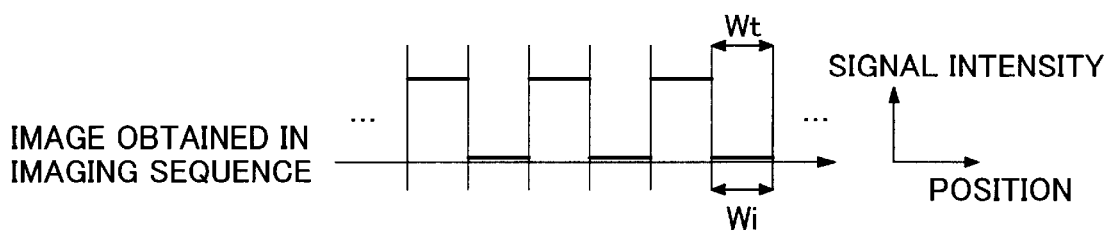
Figure 8C:
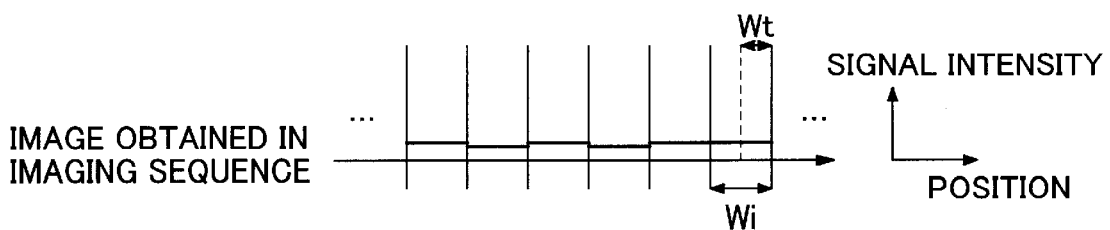

FIG. 8 are diagrams describing signal intensity profiles in an MRI image due to a tagging sequence which applies the amplitude modulated burst pulse in an embodiment according to this invention. FIG. 8A is a diagram describing a signal intensity profile in an MRI image when Wt is twice Wi, FIG. 8B is a diagram describing the signal intensity profile in an MRI image when Wt and Wi are equal, and FIG. 8C is a diagram describing the signal intensity profile in an MRI image when Wt is ½ of Wi. FIG. 8 shows how the signal intensity of the tags shown in FIG. 7 appears on the MRI image. FIG. 8A corresponds to FIG. 7A, FIG. 8B corresponds to FIG. 7B and FIG. 8C corresponds to FIG. 7C.

As the signal intensity profile varies continuously in space while the pixel size is a finite value, the signal intensity profile is discretized and averaged when the echo signal is received and the image is reconstructed, and appears on the MRI image. Immediately after the tagging sequence is implemented, the signal intensity profile shown in FIG. 8 is deduced by assuming (1) the signal intensity on the periphery of bright spots is 0, and (2) the recovery of nuclear magnetization during imaging is ignored, and averaging after discretizing the signal profile of the tags by Wi.

From FIG. 8, it is seen that, when Wt is less than Wi, the signal intensity difference between the bright spots and the peripheral region is reduced by discretization and averaging. An identical phenomenon occurs when Wt is an integral multiple of Wi. When the signal intensity difference between bright spots and the periphery is small, there is a possibility that extraction of the bright spots may be difficult, so it is preferable that Wt is an integral multiple of Wi.

Figure 9A:
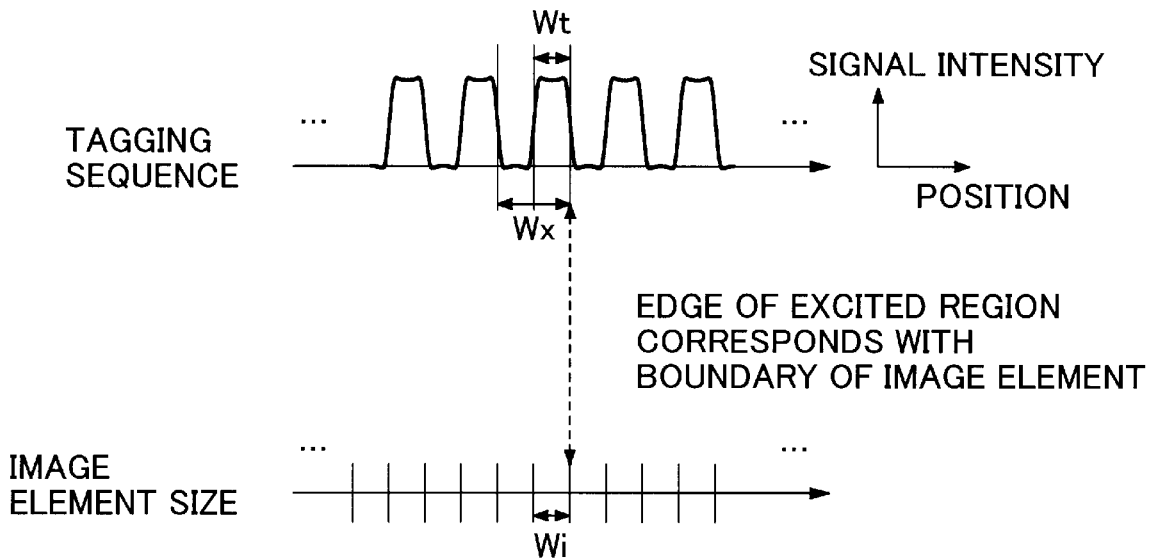
FIGS. 9A, 9B are diagrams describing the relation of an excitation profile and pixel size of MRI image in an embodiment according to this invention.
Figure 9B:
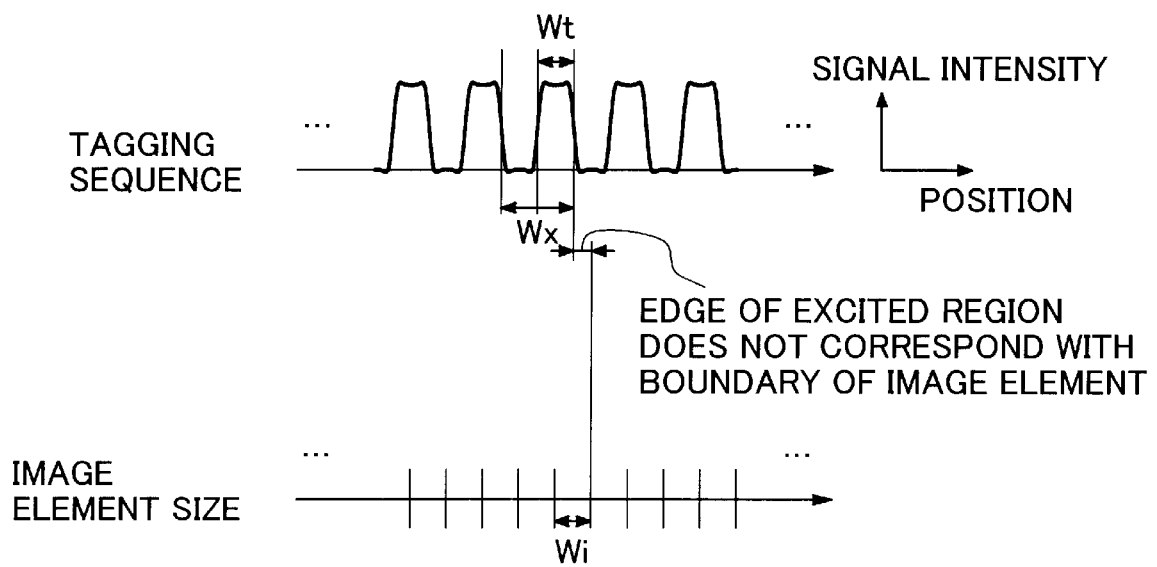

FIG. 9 is a diagram showing the relation between the excitation profile due to the tagging sequence which applies an amplitude modulated burst pulse, and the pixel size of the MRI image. FIG. 9A is a diagram describing the relation when the edge of the excited region and the boundary between pixels coincides, and FIG. 9B is a diagram describing the relation when the edge of the excited region and the boundary between pixels do not coincide.

In FIG. 9, as in the case of FIG. 7, the vertical axis shows the signal intensity and the horizontal axis shows the positional coordinates. Wt=Wi, and the edge of the excitation profile due to the tagging sequence and the boundary between pixels of the MRI image coincides in FIG. 9A, but do not coincide in FIG. 9B.

Figure 10A:
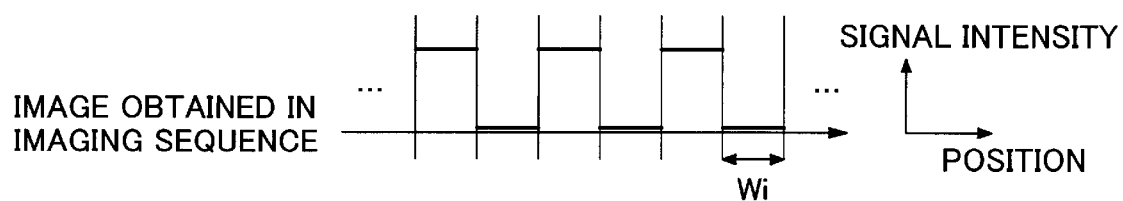
FIGS. 10A, 10B are diagrams describing a signal intensity profile in an MRI image in an embodiment according to this invention.
Figure 10B:
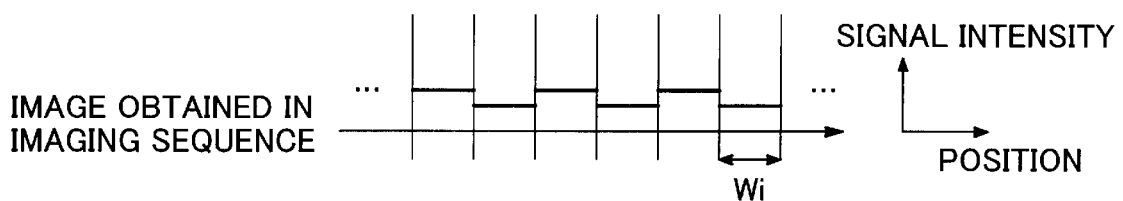

FIG. 10 is a signal intensity profile in an MRI image due to a pulse sequence which applies an amplitude modulated burst pulse in an embodiment of the invention. FIG. 10A is a diagram describing the signal intensity profile in the MRI image when the edge of the excitation area and the boundary between pixels of the MRI image coincide, and FIG. 10B is a diagram describing the signal intensity profile in the MRI image when the edge of the excitation area and the boundary between pixels of the MRI image do not coincide. FIG. 10 shows how the signal intensity of the tags shown in FIG. 9 appears on the MRI image. FIG. 10A corresponds to FIG. 9A, and FIG. 10B corresponds to FIG. 9B. As shown in FIG. 10B, when the edge of the excitation profile due to the tagging sequence and the boundary between pixels of the MRI image do not coincide, the tags are averaged spatially and the signal intensity of the tags decreases. As a result, identification of the bright spots of the tags is difficult, and this is a reason why the extraction precision of cardiac function deteriorates. As shown in FIG. 10A, when the edge of the excitation profile due to the tagging sequence and the boundary between pixels of the MRI image do coincide, the tags are not averaged spatially, and the signal intensity of the tags hardly decreases. Therefore, it is preferable to make the edge of the excitation profile due to the tagging sequence and the boundary between pixels of the MRI image coincide.

As is clear from the above description, it will be understood that the following two conditions must be satisfied regarding the relation between the excitation profile due to tagging and the size of pixels of the MRI image in order to improve the extraction precision of cardiac functions.

(Condition 1) Wt is an integral multiple of Wi.

(Condition 2) The edge of the excitation profile due to the tagging sequence and the boundary between pixels of the MRI image coincide.

The deduction of the imaging conditions required to satisfy these two conditions will now be described. It will be assumed that the field of view in the imaging sequence and the field of view in the tagging sequence are identical. First, the method of deducing parameters of the pulse sequence for satisfying (Condition 1) will be described. When the amplitude modulated burst pulse is applied, the ratio of the width Wt and the interval Wx of the excitation area has a 1:1: correspondence with the excitation frequency, and in the series of imaging sequences which apply amplitude modulated burst pulses having m excitation frequencies, Wt:Wx= 1:m. Wi is determined by the intensity of the read-out gradient magnetic field applied when the echo signal is measured, the sampling period and the number of sampling points. Therefore, Wt which is an integral multiple of Wi can also be made to correspond with the parameters when the echo signal is measured in the imaging sequence in the same way as Wi.

Figure 11:
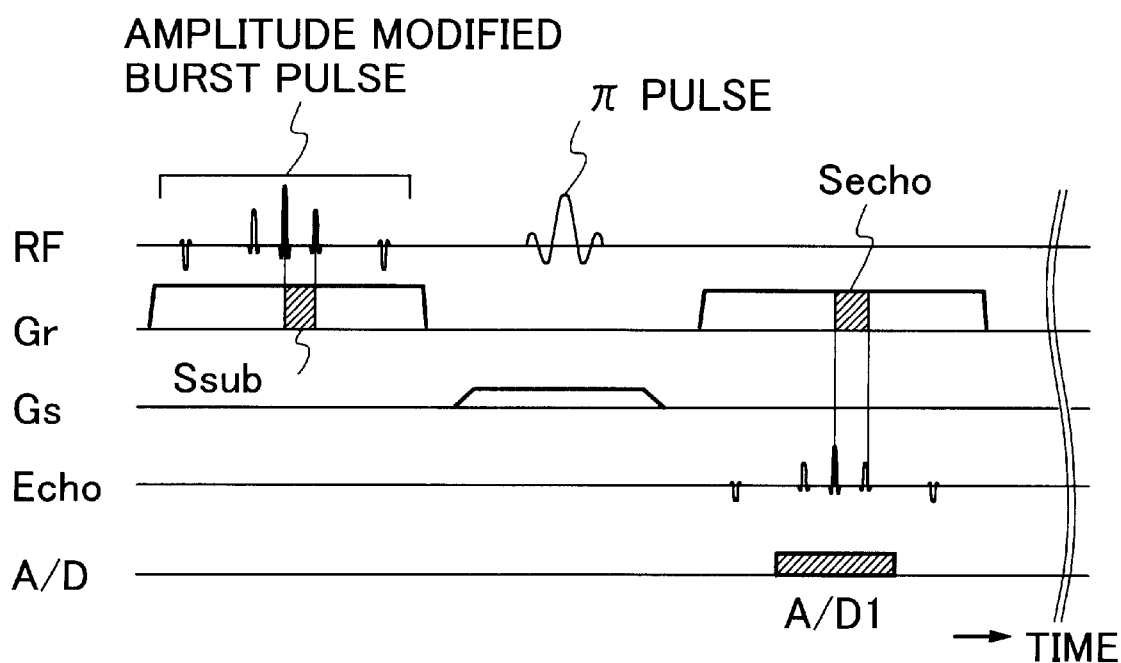
FIG. 11 is a diagram describing the relation of an applied amount of a readout gradient magnetic field when an amplitude modulated burst pulse is applied, and an applied amount of a readout gradient magnetic field when an echo signal is measured.

FIG. 11 is a diagram describing the relation between the applied amount of the read-out gradient magnetic field when an amplitude modulated burst pulse is applied, and the applied amount of the read-out gradient magnetic field when the echo signal is measured, in an embodiment of this invention. As shown in FIG. 11, an applied amount Ssub of the read-out gradient magnetic field which is applied between peaks of adjacent sub-pulses of the amplitude modulated burst pulse is equal to an applied amount Secho of the read-out gradient magnetic field applied between peaks of adjacent echo signals (Ssub=Secho). The applied amount of the gradient magnetic field is the product of the intensity and application time of the gradient magnetic field.

Figure 12:
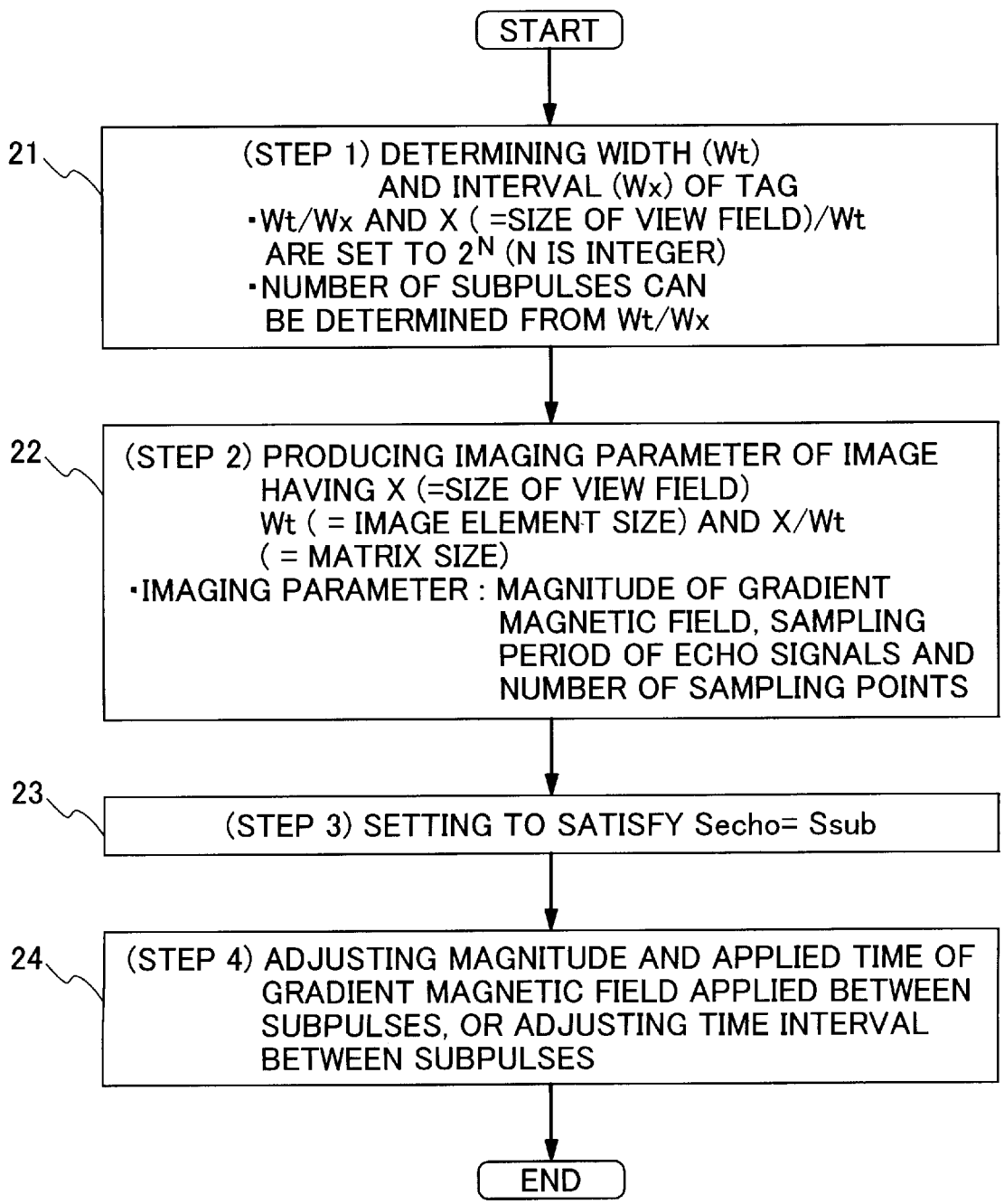
FIG. 12 is a diagram describing the procedure for deducing parameters in a pulse sequence which applies an amplitude modulated burst pulse in an embodiment according to this invention.

FIG. 12 is a diagram describing the procedure for deducing parameters in a pulse sequence which applies an amplitude modulated burst pulse in an embodiment of this invention.

(Step 1)

The width Wt of the tags and an interval Wx between tags are determined. At this time, the ratio=Wt/Wx and the ratio=X (field of view) /Wt are taken as a number of exponentiations of 2. From the values of Wt, Wx, the value of n in the amplitude modulated burst pulse having n excitation frequencies is determined. Also, the number of sub-pulses in the amplitude modulated burst pulse having n excitation frequencies applied in the series of imaging sequences is (4n—3) (not including sub-pulses of amplitude 0), so the number of sub-pulses can also be determined.

(Step 2)

Imaging parameters of the image (intensity of readout gradient magnetic field, echo signal sampling period and number of echo signal sampling points) wherein the field of view is X and pixel size is Wt, and the matrix size is X/Wt, in the imaging sequence and tagging sequence, are deduced. Deduction of the parameters in (Step 2) is identical to the method of deducing parameters in ordinary imaging.

(Step 3)

The applied amount Secho of the read-out gradient magnetic field applied between peaks of adjacent echo signals, and the applied amount Ssub of the read-out gradient magnetic field applied between peaks of adjacent sub-pulses of the amplitude modulated burst pulse, are set equal.

(Step 4)

When there are hardware restrictions such as the maximum output of the radiofrequency magnetic field, the intensity and application time of the read-out gradient magnetic field applied between peaks of adjacent sub-pulses in the amplitude modulated burst pulse, or a peak time interval of these sub-pulses, may also be adjusted.

The procedure for deducing parameters in the pulse sequence which applies the amplitude modulated burst pulse described above can also be applied to the tagging sequence or the imaging sequence, and the parameters of the imaging sequence can also be used as the parameters of the tagging sequence. Hereafter, the procedure for deducing parameters will be shown using specific examples.

Figure 13:
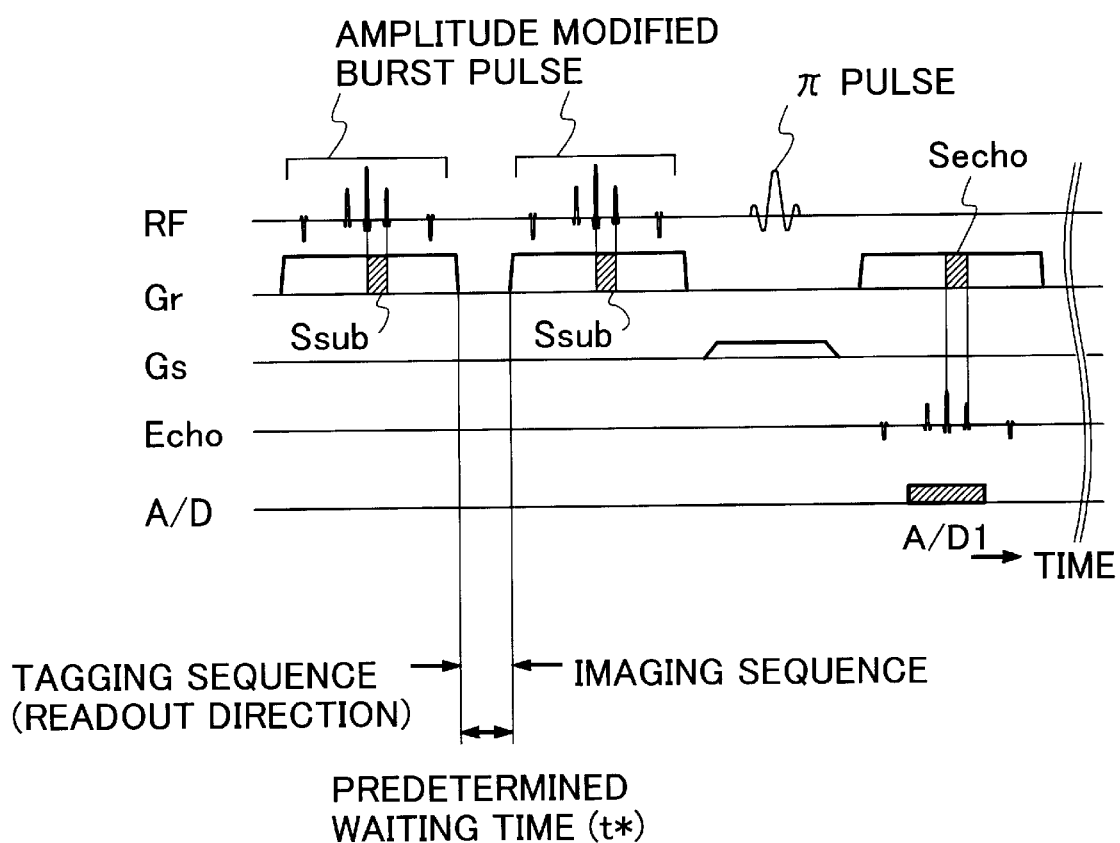
FIG. 13 is a diagram describing a pulse sequence having a tagging sequence and an imaging sequence wherein the width of excitation areas and the interval between excitation areas is the same, in an embodiment according to this invention.

FIG. 13 is a diagram describing a pulse sequence which makes the width of the excitation area and interval between excitation areas in the tagging sequence and imaging sequence which apply the amplitude modulated burst pulse the same for the tagging sequence and imaging sequence. Here, the ratio of the width (Wt1) and interval (Wx1) of the excitation area due to the tagging sequence is Wt1:Wx1=1:2, the ratio of the width (Wti1) and interval (Wxi1) of the excitation area in the acquired image is Wti1:Wxi1=1:2, it is assumed that Wt1=Wti1, and the parameters related to the tagging sequence are deduced. From the conditions regarding the width and interval of the excitation area, a series of imaging sequences is performed comprising application of the amplitude modulated burst pulse having two excitation frequencies as shown in FIG. 25. As Wt1=Wti1, the parameters related to the application of the amplitude modulated burst pulse in the imaging sequence can be applied to the parameters related to application of the amplitude modulated burst pulse in the tagging sequence as they are.

Figure 14A:
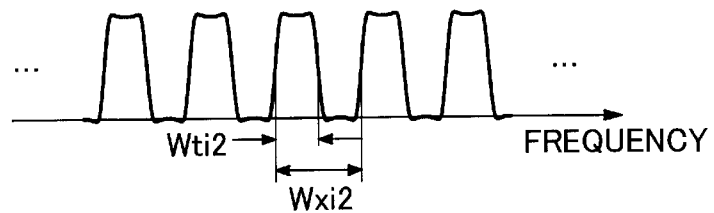
FIGS. 14A, 14B and 14C are diagrams describing a width, an interval and a pulse sequence in an excitation area in an embodiment according to this invention.
Figure 14B:
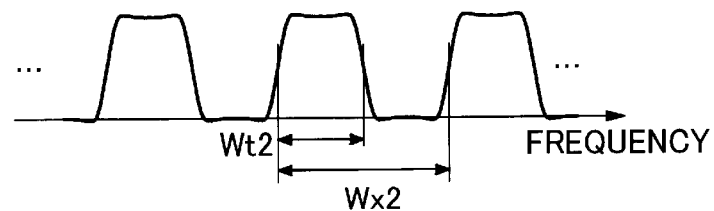

FIG. 14 is a diagram describing a width (Wti2) and interval (Wxi2) of the excitation area due to the imaging sequence (FIG. 14A), a width (Wt2) and interval (Wx2) of the excitation area due to the tagging sequence (FIG. 14B), and the pulse sequence when the width and interval of the excitation area due to the tagging sequence and imaging sequence which apply the amplitude modulated burst pulse are different for the tagging sequence and imaging sequence in an embodiment of this invention. FIG. 14A shows the signal intensity profile on the acquired image, and FIG. 14B shows the signal intensity profile of the tags. Here, Wt2= 2×Wti2, and Wx2=2×Wt2=2×Wxi2. The parameters relating to the tagging sequence in this case will be deduced.

First, as the width and interval of the excitation area due to the tagging sequence may both be considered as double the width and interval of the excitation area due to the imaging sequence, imaging conditions may be considered which acquire an image that doubles the size of pixels.

From the correspondence relations between pixel size, intensity of the read-out gradient magnetic field when the echo signal is measured, sampling period and number of sampling points, if the amplitude of the read-out gradient magnetic field is set constant and the number of sampling points is halved, the imaging condition wherein the pixel size is doubled, is obtained. In other words, by making the applied amount Ssub' of the gradient magnetic field between peaks of adjacent sub-pulses in the amplitude modulated burst pulse applied in the tagging sequence, ½ of the applied amount Secho of the read-out gradient magnetic field applied in the imaging sequence, tags which satisfy the relations Wt2=2×Wti2, and Wx2=2×Wt2=2×Wxi2 can be assigned. To satisfy the relation Ssub'=Secho/2, the peak interval of adjacent sub-pulses of the amplitude modulated burst pulse may be for example be set to ½, and the amplitude of the read-out gradient magnetic field applied between peaks of adjacent sub-pulses may be set to ½.

Figure 14C:
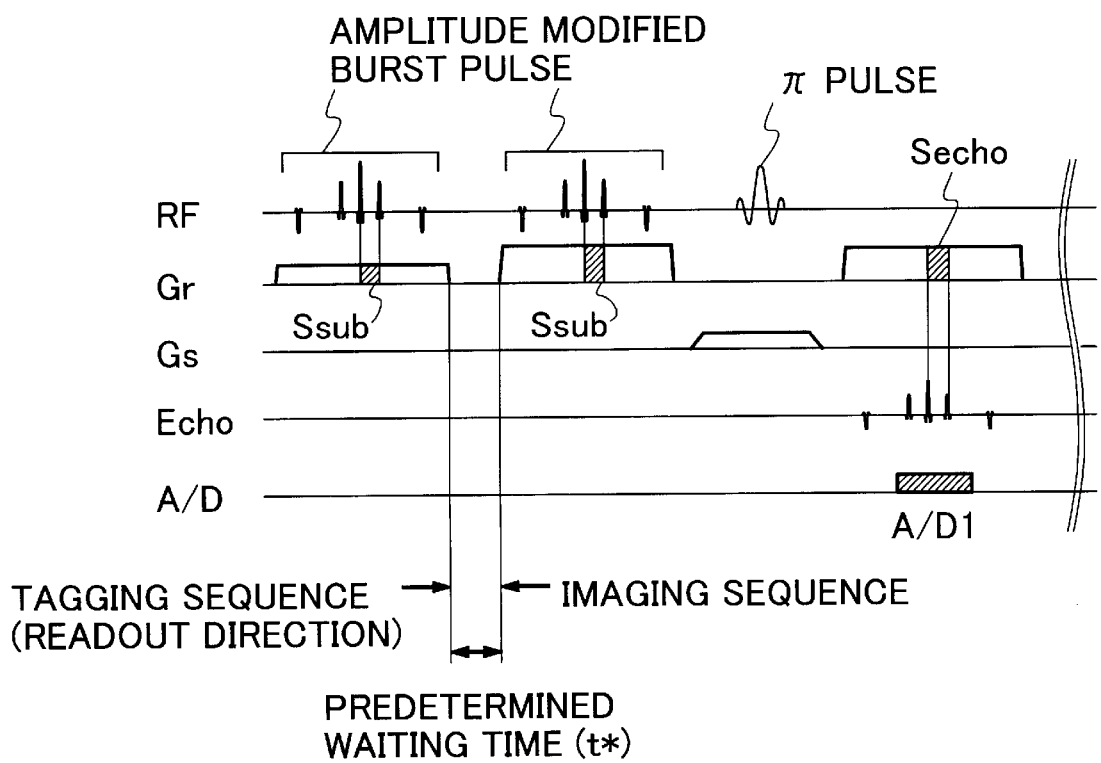

FIG. 14C shows the pulse sequence using the aforesaid deduced parameters. In the pulse sequence shown in FIG. 14C, with the amplitude of the read-out gradient magnetic field applied between peaks of adjacent sub-pulses of the amplitude modulated burst pulse as ½, the width and interval of the excitation area due to the tagging sequence and imaging sequence are arranged to differ.

The method of deducing the parameters relating to the pulse sequence above was described for the case of a pulse sequence comprising an amplitude modulated burst pulse having two excitation frequencies shown in FIG. 25, but it can be extended to the case where the number of sub-pulses of the amplitude modulated burst pulse applied in the tagging sequence is n, and the number of sub-pulses of the amplitude modulated burst pulse applied in the imaging sequence is m (n, m are respectively numbers of exponentiations of 2).

In the above description, assignment of tags in the readout direction was described, however parameters can be deduced by an identical procedure for tag assignment in the phase encoding direction. To make the width of tags and interval between tags the same in the readout direction and phase encoding direction, the parameters may be deduced taking the field of view in the imaging sequence and the field of view in the tagging sequence as rectangular.

The above is a description of the method of deducing parameters in a pulse sequence satisfying (Condition 1). Next, the method of deducing parameters in a pulse sequence satisfying (Condition 2) will be described.

Figure 24:
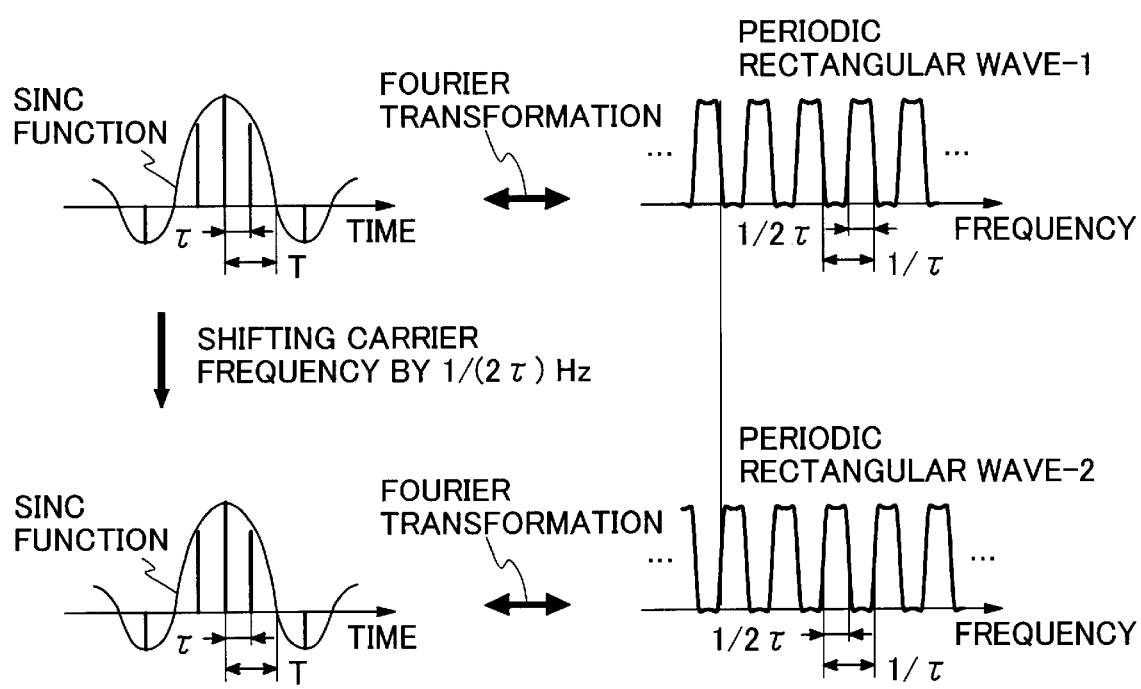
FIG. 24 is a diagram describing the relation of an amplitude modulated burst pulse shown in FIG. 22 in real space and frequency space, and the correspondence relation between excitation frequency and excitation areas in the application of an amplitude modulated burst pulse using two excitation frequencies (prior art).

The position of the excitation region may be shifted by modifying the carrier frequency of the amplitude modulated burst pulse, as shown in FIG. 24. Therefore, (Condition 2) can be realized by controlling the carrier frequency by a tagging sequence and imaging sequence.

Figure 15A:
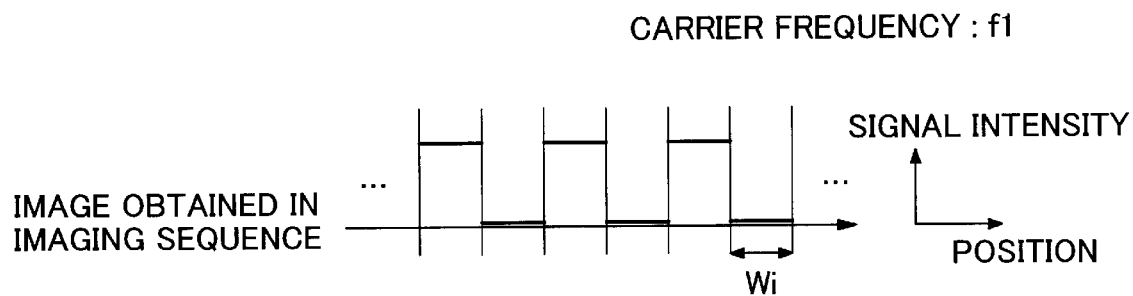
FIGS. 15A, 15B and 15C are diagrams describing the variation of a signal intensity profile, and a simple method of deducing an optimum carrier frequency, in an embodiment according to this invention.
Figure 15B:
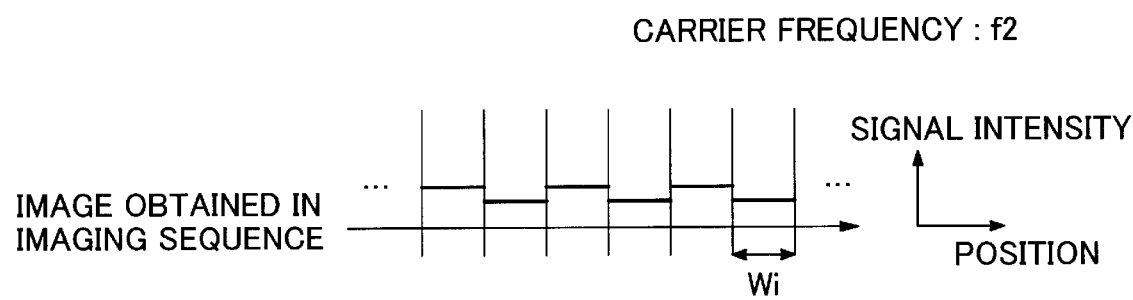
Figure 15C:
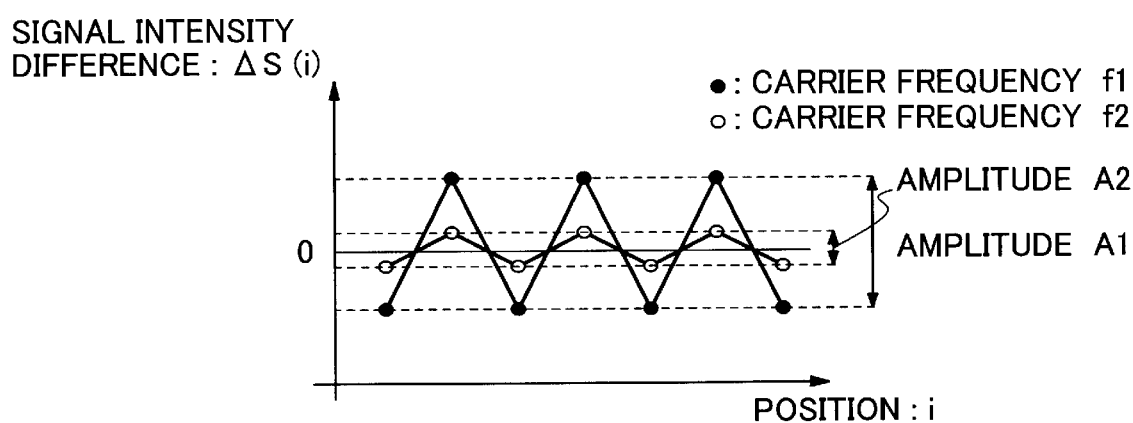

FIG. 15 shows diagrams relating to the case when the excitation region is shifted by modifying the carrier frequency of the amplitude modulated burst pulse in the embodiment according to this invention, i.e., a signal intensity profile when the edges of the tags and the boundaries between pixels coincide (FIG. 15A), the signal intensity profile when the edges of the tags and the boundaries between pixels do not coincide (FIG. 15B), and a diagram describing the simplest method of deducing the optimum carrier frequency to make the edges of the tags and boundaries between pixels coincide (FIG. 15C).

First, the image is acquired taking the carrier frequency of the tagging sequence as a predetermined value f1, as shown in FIG. 15A. Next, the carrier frequency is slightly shifted to f2, and the image is acquired, as shown in FIG. 15B. The signal intensity profile on the acquired image has different distributions in FIG. 15A and FIG. 15B corresponding to the positional relation between the edges of the signal intensity profiles of the tags and the boundaries between pixels of the acquired image. The carrier frequency in the tagging sequence can be optimized by referring to these distributions.

Regarding the reconstructed images obtained by modifying the carrier frequency, differences of signal intensities are calculated between adjacent pixels in the direction in which the tags are assigned. This calculation is implemented by Equation (1), taking the positional coordinates in the direction in which tags are assigned as i, the signal intensity of the pixel at the position coordinate i as $S(i)$, the difference of signal-intensities as $\delta S(i)$, and the number of pixels as N, where $1<i<(N-1)$. The brightness of the tags becomes more blurred the smaller the difference of signal intensity in the tagged region and the surrounding region.

$$\Delta S(i)=S(i+1)-S(i) \quad (1)$$

FIG. 15C shows the results of applying Equation (1) to FIG. 15A and FIG. 15B. The amplitude A1 of the signal difference $\delta S(i)$ becomes a maximum in the case of the carrier frequency f1 when the edges of the tags coincide with the boundaries between pixels, as is clear from FIG. 15C. Conversely, when the amplitude of the signal difference $\delta S(i)$ is a maximum, it can be determined that the edges of the tags coincide with the boundaries between pixels. Due to the above procedure, (Condition 2) can be realized.

Another way of shifting the excitation region is to modify the phase of the sub-pulse.

Figure 16A:
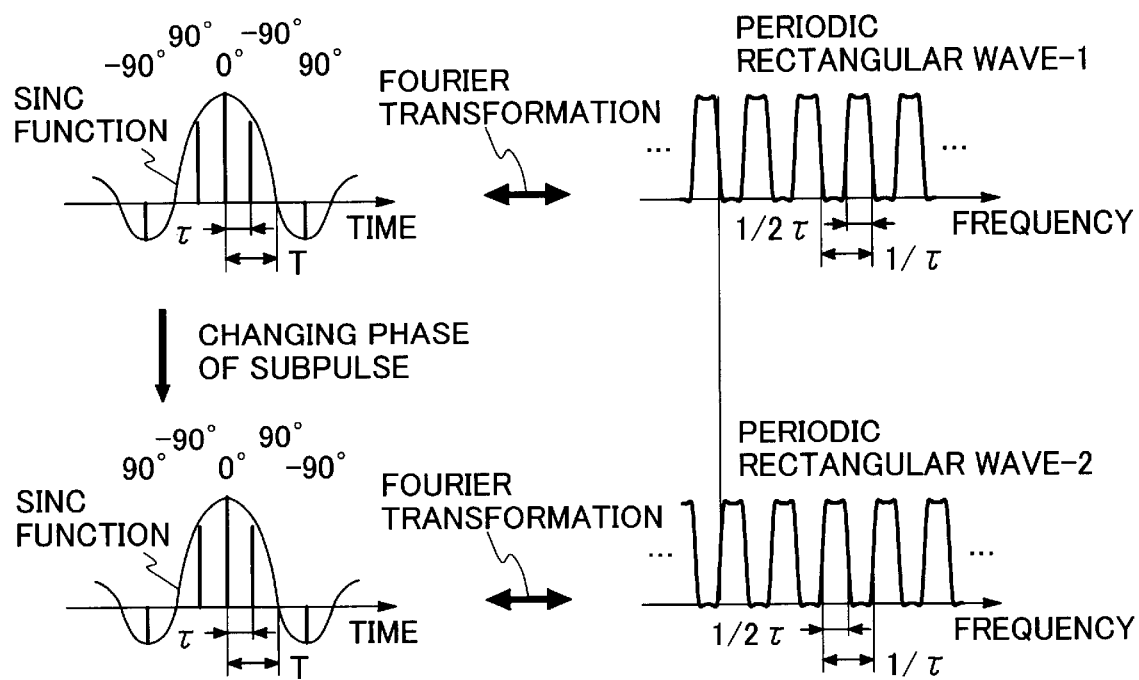
FIGS. 16A, 16B are diagrams describing the relation of a phase value of sub-pulses of an amplitude modulated burst pulse and excitation areas, and a method of deducing the phase value of the sub-pulses of the amplitude modulated burst pulse, in an embodiment according to this invention.
Figure 16B:
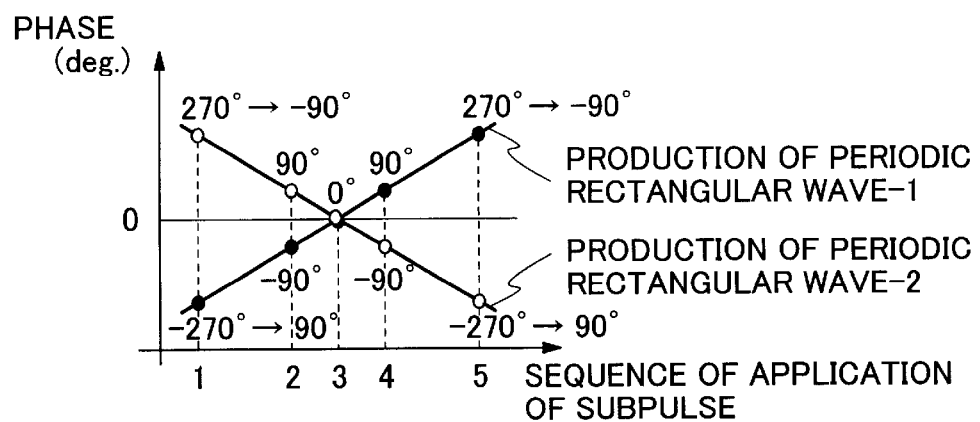
Figure 17A:
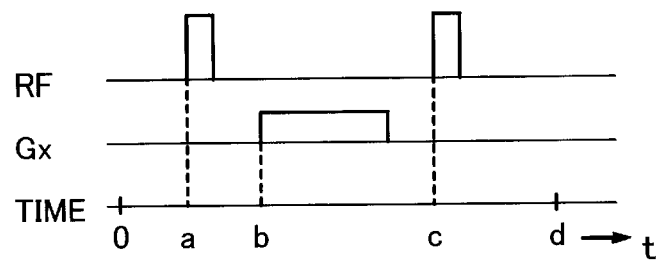
FIGS. 17A, 17B and 17C are diagrams describing the principle of assigning tags in the prior art.
Figure 17B:
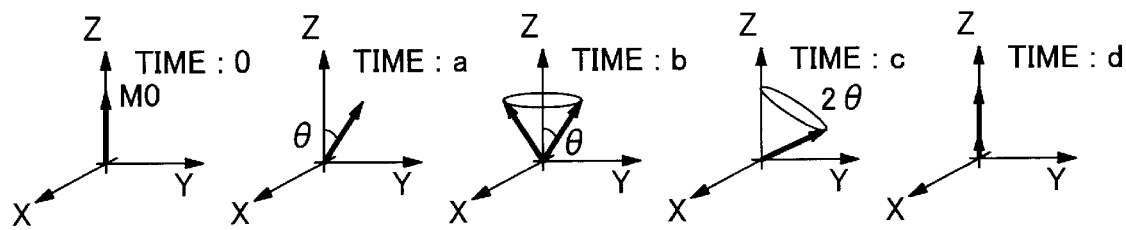
Figure 17C:
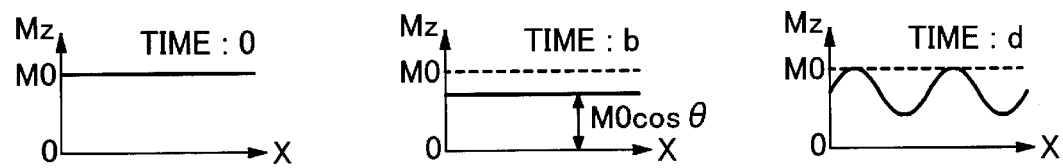
Figure 18:
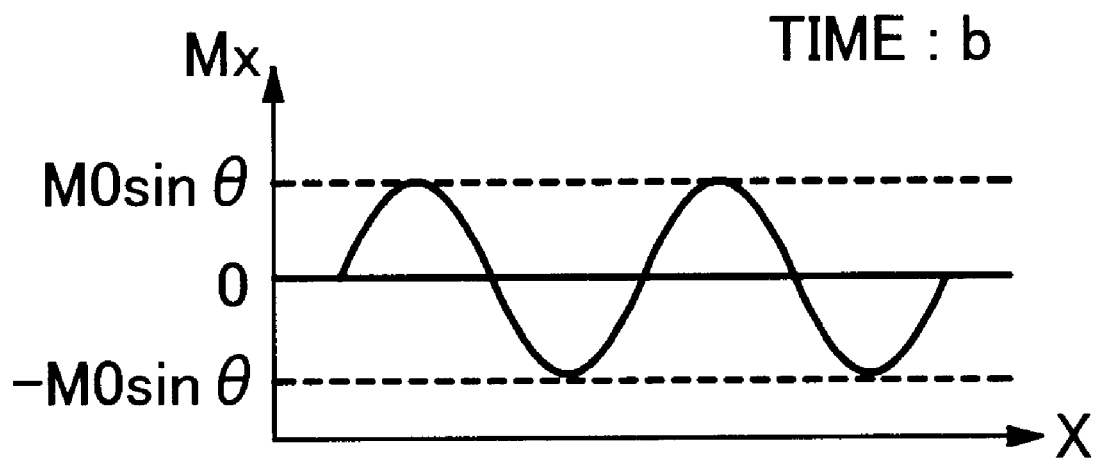
FIG. 18 is a diagram describing the intensity of an x direction component of a nuclear magnetization vector in a tagging sequence according to the prior art.

FIG. 16 shows the relation between the phase value of a sub-pulse of the amplitude modulated burst pulse and the excitation region (FIG. 16A), and a diagram describing a method of deducing the phase value of the sub-pulse of the amplitude modulated burst pulse (FIG. 16B). By modifying the phase of the sub-pulse of the amplitude modulated burst pulse from (−90°, 90°, 0°, −90°, 90°) to (90°, −90°, 90°, −90°), the phase of the excitation region is shifted, and the excitation region changes, as shown in FIG. 16A. FIG. 16B is a graph representing the phase shift of the sub-pulse of the amplitude modulated burst pulse in another form. The horizontal axis of FIG. 16B shows the applied sequence of sub-pulses. However, including the point where the amplitude is 0, the interval of the applied sequence 1 and 2, and the interval of the applied sequence 4 and 5, are considered to be time intervals which are twice the intervals of other applied sequences. The vertical axis of FIG. 16B is the phase of the sub-pulse.

From FIG. 16B, it is seen that a directly proportional relation between the phase of the sub-pulse and time exists when the excitation region is shifted by modifying the phase of the sub-pulse. Further, the shifting of the excitation region by modifying the phase is the same as fixing the point (0° in the example shown in FIG. 16) of the phase of the sub-pulse at the center of the amplitude modulated burst pulse, rotating the line representing the time variation of the phase of the sub-pulse around the point of the phase of the sub-pulse at the fixed center, and modifying the inclination angle of the line.

Therefore, (Condition 2) can be represented by the following procedure. First, the phase of each sub-pulse is deduced with the above inclination angle as a predetermined value, and the image is acquired using deduced parameters. Next, the above inclination angle is slightly shifted, and image acquisition is performed. The remainder of the procedure is identical to the case where the excitation region is shifted by modifying the carrier frequency. By the above procedure, (Condition 2) can be realized even when the excitation region is shifted by modifying the phase of the sub-pulse.

What is claimed is:

1. A nuclear magnetic resonance imaging apparatus, comprising:

static magnetic field generating means for generating a static magnetic field;

gradient magnetic field generating means for generating a gradient magnetic field in three directions which are mutually perpendicular to one another;

radiofrequency magnetic field generating means for generating a radiofrequency magnetic field;

signal detecting means for detecting a nuclear magnetic resonance signal generated by a subject to be inspected;

physiological signal detecting means for detecting a periodic physiological signal generated by the subject to be inspected; and control means for controlling the gradient magnetic field generating means, the radiofrequency magnetic field generating means, the signal detecting means, and the physiological signal detecting means to:

(1) detect the periodic physiological signal, and generate, from the periodic physiological signal, a synchronizing signal which initiates a pulse sequence for detecting the nuclear magnetic resonance signal; and (2) apply to the subject to be inspected, in synchronism with the synchronizing signal, a radiofrequency burst pulse including plural sub-pulses which are formed at equidistant intervals on a time axis and which have amplitudes modulated by a sinc function, and apply to the subject to be inspected, in synchronism with the synchronizing signal, the gradient magnetic field in one direction of the three directions, wherein the radiofrequency burst pulse is applied to the subject to be inspected while the gradient magnetic field in the one direction is being applied to the subject to be inspected to modulate nuclear magnetizations of the subject to be inspected in the one direction.

2. A nuclear magnetic resonance imaging apparatus, comprising:

static magnetic field generating means for generating a static magnetic field;

gradient magnetic field generating means for generating a gradient magnetic field in a first direction, a second direction, and a third direction which are mutually perpendicular to one another;

radiofrequency magnetic field generating means for generating a radiofrequency magnetic field;

signal detecting means for detecting a nuclear magnetic resonance signal generated by the subject to be inspected;

physiological signal detecting means for detecting a periodic physiological signal generated by the subject to be inspected; and control means for controlling the gradient magnetic field generating means, the radiofrequency magnetic field generating means, the signal detecting means, and the physiological signal detecting means to:

(1) detect the periodic physiological signal, and generate, from the periodic physiological signal, a synchronizing signal which initiates a pulse sequence for detecting the nuclear magnetic resonance signal;

(2) apply to the subject to be inspected, in synchronism with the synchronizing signal, a first radiofrequency burst pulse including plural sub-pulses which are formed at equidistant intervals on a time axis and which have amplitudes modulated by a sinc function, and apply to the subject to be inspected, in synchronism with the synchronizing signal, the gradient magnetic field in the first direction, wherein the first radiofrequency burst pulse is applied to the subject to be inspected while the gradient magnetic field in the first direction is being applied to the subject to be inspected to modulate nuclear magnetizations of the subject to be inspected in the first direction; and (3) after (2) has been completed, apply to the subject to be inspected a second radiofrequency burst pulse including plural sub-pulses which are formed at equidistant intervals on the time axis and which have amplitudes modulated by a sinc function, and apply to the subject to be inspected the gradient magnetic field in the second direction, wherein the second radiofrequency burst pulse is applied to the subject to be inspected while the gradient magnetic field in the second direction is being applied to the subject to be inspected to modulate the nuclear magnetizations of the subject to be inspected in the second direction.

3. A nuclear magnetic resonance imaging apparatus, comprising:

static magnetic field generating means for generating a static magnetic field;

gradient magnetic field generating means for generating a gradient magnetic field in a first direction, a second direction, and a third direction which are mutually perpendicular to one another;

radiofrequency magnetic field generating means for generating a radiofrequency magnetic field;

signal detecting means for detecting a nuclear magnetic resonance signal generated by the subject to be inspected;

physiological signal detecting means for detecting a periodic physiological signal from the subject to be inspected; and control means for controlling the gradient magnetic field generating means, the radiofrequency magnetic field generating means, the signal detecting means, and the physiological signal detecting means to:

(1) detect the periodic physiological signal, and generate, from the periodic physiological signal, a synchronizing signal which initiates a pulse sequence for detecting the nuclear magnetic resonance signal;

(2) apply to the subject to be inspected, in synchronism with the synchronizing signal, a first radiofrequency burst pulse including plural sub-pulses which are formed at equidistant intervals on a time axis and which have amplitudes are modulated by a sinc function, and apply to the subject to be inspected, in synchronism with the synchronizing signal, the gradient magnetic field in one of the first direction and the second direction, wherein the first radiofrequency burst pulse is applied to the subject to be inspected while the gradient magnetic field in the one of the first direction and the second direction is being applied to the subject to be inspected to modulate nuclear magnetizations of the subject to be inspected in the one of the first direction and the second direction;

(3) after a predetermined waiting time has elapsed after (2) has been completed, apply to the subject to be inspected a second radiofrequency burst pulse including plural sub-pulses which are formed at equidistant intervals on the time axis and which have amplitudes modulated by a sinc function, and apply to the subject to be inspected the gradient magnetic field in the first direction, wherein the second radiofrequency burst pulse is applied to the subject to be inspected while the gradient magnetic field in the first direction is being applied to the subject to be inspected to excite the nuclear magnetizations of the subject to be inspected;

(4) after (3) has been completed, apply to the subject to be inspected a radiofrequency magnetic field pulse, and apply to the subject to be inspected the gradient magnetic field in the third direction, wherein the radiofrequency magnetic field pulse is applied to the subject to be inspected while the gradient magnetic field in the third direction is being applied to the subject to be inspected;

(5) after (4) has been completed, applies to the subject to be inspected the gradient magnetic field in the second direction to assign positional information in the second direction to the nuclear magnetizations of the subject to be inspected, applies to the subject to be inspected the gradient magnetic field in the first direction to assign positional information in the first direction to the nuclear magnetizations of the subject to be inspected, cause the subject to be inspected to generate the nuclear magnetic resonance signal, and measure the nuclear magnetic resonance signal;

(6) repeat (4) and (5) plural times; and (7) repeat (1) to (6) plural times.

4. A nuclear magnetic resonance imaging apparatus according to claim 3, wherein the periodic physiological signal is a periodic physiological signal based on respiration or heartbeat of the subject to be inspected.

5. A nuclear magnetic resonance imaging apparatus according to claim 3, wherein (7) is implemented when the predetermined waiting time is constant.

6. A nuclear magnetic resonance imaging apparatus according to claim 3, wherein the predetermined waiting time is varied each time (1) to (6) of (7) are repeated.

7. A nuclear magnetic resonance imaging apparatus according to claim 3, wherein the nuclear magnetizations of the subject to be inspected in a rectangular periodic region are excited, and the width of the rectangular periodic region is larger than the size of the pixels of the image reconstructed from the nuclear magnetic resonance signal.

8. A nuclear magnetic resonance imaging apparatus according to claim 3, wherein the nuclear magnetizations of the subject to be inspected in a rectangular periodic region are excited, and the width of the rectangular periodic region is an integral multiple of the size of the pixels of the image reconstructed from the nuclear magnetic resonance signal.

9. A nuclear magnetic resonance imaging apparatus according to claim 3, wherein the nuclear magnetizations of the subject to be inspected in a rectangular periodic region are excited, and the edge of the rectangular periodic region coincides with a boundary line between the pixels of the image reconstructed from the nuclear magnetic resonance signal.

10. A nuclear magnetic resonance imaging apparatus, comprising:

static magnetic field generating means for generating a static magnetic field;

gradient magnetic field generating means for generating a gradient magnetic field in a first direction, a second direction, and a third direction which are mutually perpendicular to one another;

radiofrequency magnetic field generating means for generating a radiofrequency magnetic field;

signal detecting means for detecting a nuclear magnetic resonance signal generated by the subject to be inspected;

physiological signal detecting means for detecting a periodic physiological signal from the subject to be inspected; and control means for controlling the gradient magnetic field generating means, the radiofrequency magnetic field generating means, the signal detecting means, and the physiological signal detecting means to:

(1) detect the periodic physiological signal, and generate, from the periodic physiological signal, a synchronizing signal which initiates a pulse sequence for detecting the nuclear magnetic resonance signal;

(2) apply to the subject to be inspected, in synchronism with the synchronizing signal, a first radiofrequency burst pulse including plural sub-pulses which are formed at equidistant intervals on a time axis and which have amplitudes modulated by a sinc function, and apply to the subject to be inspected, in synchronism with the synchronizing signal, the gradient magnetic field in the first direction, wherein the first radiofrequency burst pulse is applied to the subject to be inspected while the gradient magnetic field in the first direction is being applied to the subject to be inspected to modulate nuclear magnetizations of the subject to be inspected in the first direction;

(3) after (2) has been completed, apply to the subject to be inspected a second radiofrequency burst pulse including plural sub-pulses which are formed at equidistant intervals on the time axis and which have amplitudes modulated by a sinc function, and apply to the subject to be inspected the gradient magnetic field in the second direction, wherein the second radiofrequency burst pulse is applied to the subject to be inspected while the gradient magnetic field in the second direction is being applied to the subject to be inspected to modulate the nuclear magnetizations of the subject to be inspected in the second direction;

(4) after a predetermined waiting time has elapsed after (3) has been completed, apply to the subject to be inspected a third radiofrequency burst pulse including plural sub-pulses which are formed at equidistant intervals on the time axis and which have amplitudes modulated by a sinc function, and apply to the subject to be inspected the gradient magnetic field in the first direction, wherein the third radiofrequency burst pulse is applied to the subject to be inspected while the gradient magnetic field in the first direction is being applied to the subject to be inspected to excite the nuclear magnetizations of the subject to be inspected;

(5) after (4) has been completed, apply to the subject to be inspected a radiofrequency magnetic field pulse, and apply to the subject to be inspected the gradient magnetic field in the third direction, wherein the radiofrequency magnetic field pulse is applied to the subject to be inspected while the gradient magnetic field in the third direction is being applied to the subject to be inspected;

(6) after (5) has been completed, applies to the subject to be inspected the gradient magnetic field in the second direction to assign positional information in the second direction to the nuclear magnetizations of the subject to be inspected, applies to the subject to be inspected the gradient magnetic field in the first direction to assign positional information in the first direction to the nuclear magnetizations of the subject to be inspected, cause the subject to be inspected to generate the nuclear magnetic resonance signal, and measure the nuclear magnetic resonance signal;

(7) repeat (5) and (6) plural times; and (8) repeat (1) to (7) plural times.

11. A nuclear magnetic resonance imaging apparatus according to claim 10, wherein the periodic physiological signal is a periodic physiological signal based on respiration or heartbeat of the subject to be inspected.

12. A nuclear magnetic resonance imaging apparatus according to claim 10, wherein (8) is implemented when the predetermined waiting time is constant.

13. A nuclear magnetic resonance imaging apparatus according to claim 10, wherein the predetermined waiting time is varied each time (1) to (7) of (8) are repeated.

14. A nuclear magnetic resonance imaging apparatus according to claim 10, wherein the nuclear magnetizations of the subject to be inspected in a rectangular periodic region are excited, and the width of the rectangular periodic region is larger than the size of the pixels of the image reconstructed from the nuclear magnetic resonance signal.

15. A nuclear magnetic resonance imaging apparatus according to claim 10, wherein the nuclear magnetizations of the subject in a rectangular periodic region are excited, and the width of the rectangular periodic region is an integral multiple of the size of the pixels of the image reconstructed from the nuclear magnetic resonance signal.

16. A nuclear magnetic resonance imaging apparatus according to claim 10, wherein the nuclear magnetizations of the subject to be inspected in a rectangular periodic region are excited, and the edge of the rectangular periodic region coincides with a boundary line between the pixels of the image reconstructed from the nuclear magnetic resonance signal.

17. A nuclear magnetic resonance imaging method, comprising the steps of:

(1) detecting a periodic physiological signal generated by a subject to be inspected;

(2) generating, from the periodic physiological signal, a synchronizing signal which initiates a pulse sequence for detecting a nuclear magnetic resonance signal generated by the subject to be inspected; and (3) applying to the subject to be inspected, in synchronism with the synchronizing signal, a first radiofrequency burst pulse including plural sub-pulses which are formed at equidistant intervals on a time axis and which have amplitudes modulated by a sinc function, and applying to the subject to be inspected, in synchronism with the synchronizing signal, a gradient magnetic field in one direction of three directions which are mutually perpendicular to one another, wherein the first radiofrequency burst pulse is applied to the subject to be inspected while the gradient magnetic field in the one direction is being applied to the subject to be inspected to modulate nuclear magnetizations of the subject to be inspected in the one direction.

18. A nuclear magnetic resonance imaging method, comprising the steps of:

(1) detecting a periodic physiological signal generated by a subject to be inspected;

(2) generating, from the periodic physiological signal, a synchronizing signal which initiates a pulse sequence for detecting a nuclear magnetic resonance signal generated by the subject to be inspected;

(3) applying to the subject to be inspected, in synchronism with the synchronizing signal, a first radiofrequency burst pulse including plural sub-pulses which are formed at equidistant intervals on a time axis and which have amplitudes modulated by a sinc function, and applying to the subject to be inspected, in synchronism with the synchronizing signal, a gradient magnetic field in a first direction, wherein the first radiofrequency burst pulse is applied to the subject to be inspected while the gradient magnetic field in the first direction is being applied to the subject to be inspected to modulate nuclear magnetizations of the subject to be inspected in the first direction; and (4) after the step (3) has been completed, applying to the subject to be inspected a second radiofrequency burst pulse including plural sub-pulses which are formed at equidistant intervals on the time axis and which have amplitudes modulated by a sinc function, and applying to the subject to be inspected a gradient magnetic field in a second direction, the first direction and the second direction being mutually perpendicular to one another, wherein the second radiofrequency burst pulse is applied to the subject to be inspected while the gradient magnetic field in the second direction is being applied to the subject to be inspected to modulate the nuclear magnetizations of the subject to be inspected in the second direction.

19. A nuclear magnetic resonance imaging method, comprising the steps of:

(1) detecting a periodic physiological signal generated by a subject to be inspected;

(2) generating, from the periodic physiological signal, a synchronizing signal which initiates a pulse sequence for detecting a nuclear magnetic resonance signal generated by the subject to be inspected;

(3) applying to the subject to be inspected, in synchronism with the synchronizing signal, a first radiofrequency burst pulse including plural sub-pulses which are formed at equidistant intervals on a time axis and which have amplitudes modulated by a sinc function, and applying to the subject to be inspected, in synchronism with the synchronizing signal, a gradient magnetic field in one of a first direction and a second direction which are mutually perpendicular to one another, wherein the first radiofrequency burst pulse is applied to the subject to be inspected while the gradient magnetic field in the one of the first direction and the second direction is being applied to the subject to be inspected to modulate nuclear magnetizations of the subject to be inspected in the one of the first direction and the second direction;

(4) after a predetermined waiting time has elapsed after the step (3) has been completed, applying to the subject to be inspected a second radiofrequency burst pulse including plural sub-pulses which are formed at equidistant intervals on the time axis and which have amplitudes modulated by a sinc function, and applying to the subject to be inspected a gradient magnetic field in the first direction, wherein the second radiofrequency burst pulse is applied to the subject to be inspected while the gradient magnetic field in the first direction is being applied to the subject to be inspected to excite the nuclear magnetizations of the subject to be inspected;

(5) after the step (4) has been completed, applying to the subject to be inspected a radiofrequency magnetic field pulse, and applying to the subject to be inspected a gradient magnetic field in a third direction, the first direction, the second direction, and the third direction being mutually perpendicular to one another, wherein the radiofrequency magnetic field pulse is applied to the subject to be inspected while the gradient magnetic field in the third direction is being applied to the subject to be inspected;

(6) after the step (5) has been completed, applying to the subject to be inspected the gradient magnetic field in the second direction to assign positional information in the second direction to the nuclear magnetizations of the subject to be inspected, applying to the subject to be inspected the gradient magnetic field in the first direction to assign positional information in the first direction to the nuclear magnetizations of the subject to be inspected, causing the subject to be inspected to generate the nuclear magnetic resonance signal, and measuring the nuclear magnetic resonance signal;

(7) repeating the steps (5) and (6) plural times; and (8) repeating the steps (1) to (7) plural times.

20. A nuclear magnetic resonance imaging method, comprising the steps of:

(1) detecting a periodic physiological signal generated by a subject to be inspected;

(2) generating, from the periodic physiological signal, a synchronizing signal which initiates a pulse sequence for detecting a nuclear magnetic resonance signal generated by the subject to be inspected;

(3) applying to the subject to be inspected, in synchronism with the synchronizing signal, a first radiofrequency burst pulse including plural sub-pulses which are formed at equidistant intervals on a time axis and which have amplitudes modulated by a sinc function, and applying to the subject to be inspected, in synchronism with the synchronizing signal, a gradient magnetic field in a first direction, wherein the first radiofrequency burst pulse is applied to the subject to be inspected while the gradient magnetic field in the first direction is being applied to the subject to be inspected to modulate nuclear magnetizations of the subject to be inspected in the first direction;

(4) after the step (3) has been completed, applying to the subject to be inspected a second radiofrequency burst pulse including plural sub-pulses which are formed at equidistant intervals on the time axis and which have amplitudes modulated by a sinc function, and applying to the subject to be inspected a gradient magnetic field in a second direction, the first direction and the second direction being mutually perpendicular to one another, wherein the second radiofrequency burst pulse is applied to the subject to be inspected while the gradient magnetic field in the second direction is being applied to the subject to be inspected to modulate the nuclear magnetizations of the subject to be inspected in the second direction;

(5) after a predetermined waiting time has elapsed after the step (4) has been completed, applying to the subject to be inspected a third radiofrequency burst pulse including plural sub-pulses which are formed at equidistant intervals on the time axis and which have amplitudes modulated by a sinc function, and applying to the subject to be inspected a gradient magnetic field in the first direction, wherein the third radiofrequency burst pulse is applied to the subject to be inspected while the gradient magnetic field in the first direction is being applied to the subject to be inspected to excite the nuclear magnetizations of the subject to be inspected;

(6) after the step (5) has been completed, applying to the subject to be inspected a radiofrequency magnetic field pulse, and applying to the subject to be inspected a gradient magnetic field in a third direction, the first direction, the second direction, and the third direction being mutually perpendicular to one another, wherein the radiofrequency magnetic field pulse is applied to the subject to be inspected while the gradient magnetic field in the third direction is being applied to the subject to be inspected;

(7) after the step (6) has been completed, applying to the subject to be inspected the gradient magnetic field in the second direction to assign positional information in the second direction to the nuclear magnetizations of the subject to be inspected, applying to the subject to be inspected the gradient magnetic field in the first direction to assign positional information in the first direction to the nuclear magnetizations of the subject to be inspected, causing the subject to be inspected to generate the nuclear magnetic resonance signal, and measuring the nuclear magnetic resonance signal;

(8) repeating the steps (6) and (7) plural times; and (9) repeating the steps (1) to (8) plural times.

* * * * *